(12) United States Patent
Savard et al.

(10) Patent No.: US 8,529,484 B2
(45) Date of Patent: Sep. 10, 2013

(54) ORTHOTIC FOOT BRACE

(75) Inventors: Stéphane Savard, Québec (CA);
François Côté, Québec (CA)

(73) Assignee: Ortheses Turbomed Inc./Turbomed Orthotics Inc. (CA)

( * ) Notice: Subject to any disclaimer, the term of this patent is extended or adjusted under 35 U.S.C. 154(b) by 255 days.

(21) Appl. No.: 12/702,967

(22) Filed: Feb. 9, 2010

(65) Prior Publication Data
US 2011/0196277 A1 Aug. 11, 2011

(51) Int. Cl.
| | | |
|---|---|---|
| A43B 5/00 | (2006.01) |
| A43B 7/14 | (2006.01) |
| A43B 7/20 | (2006.01) |
| A43B 23/02 | (2006.01) |
| A61F 5/37 | (2006.01) |
| A61F 13/00 | (2006.01) |
| A61F 5/00 | (2006.01) |
| A61B 19/00 | (2006.01) |

(52) U.S. Cl.
USPC ............ 602/28; 36/83; 36/88; 36/89; 36/109; 128/846; 128/869; 128/882; 602/5; 602/23; 602/25; 602/27; 602/29

(58) Field of Classification Search
USPC ................ 602/5, 23, 25–27, 28–29; 36/109, 36/83, 88–89; 128/846, 869, 882
See application file for complete search history.

(56) References Cited

U.S. PATENT DOCUMENTS

| | | | | |
|---|---|---|---|---|
| 1,332,047 | A | * | 2/1920 | Lasher ............................ 602/27 |
| 2,444,839 | A | | 7/1948 | Markkula |
| 2,525,237 | A | | 10/1950 | Park |
| 2,557,603 | A | | 6/1951 | Invidiato |
| 2,567,195 | A | | 9/1951 | Ellery |
| 2,584,010 | A | | 1/1952 | L.M. Goffredo |
| 2,663,294 | A | | 12/1953 | Harrison |
| 2,712,310 | A | | 7/1955 | Giambra |
| 2,847,991 | A | | 8/1958 | Andrews |
| 2,949,111 | A | | 8/1960 | Ruotoistenmaki |
| 3,171,407 | A | | 3/1965 | Rogers |
| 3,527,209 | A | | 9/1970 | Baker |

(Continued)

FOREIGN PATENT DOCUMENTS

| | | |
|---|---|---|
| DE | 202005000978 | 4/2005 |
| WO | 0135876 | 5/2001 |
| WO | 2006056868 | 6/2006 |

OTHER PUBLICATIONS

ToeOFF, Allard USA, Inc.

*Primary Examiner* — Patricia Bianco
*Assistant Examiner* — Brandon L Jackson
(74) *Attorney, Agent, or Firm* — Cantor Colburn LLP

(57) ABSTRACT

An orthotic foot brace for a person wearing a footwear includes: a lower leg holder; a lower leg strut extending downwardly towards the footwear; a foot strut having a rear section secured to the vertical strut, at least one of a median section and a lateral section located on a respective side of the footwear and extending outwardly thereof, and a front section securable to an instep section of the footwear; and a brace retaining member secured to the foot strut juxtaposed to the footwear, and extending from the median side of the footwear to the lateral side of the footwear, outwardly thereof, and restraining a rearwardly pivotal movement of the brace.

20 Claims, 21 Drawing Sheets

(56) References Cited

U.S. PATENT DOCUMENTS

| | | | |
|---|---|---|---|
| 3,556,091 | A | 1/1971 | Haig |
| 3,765,409 | A | 10/1973 | Merkle |
| 3,827,430 | A | 8/1974 | Fadden |
| 3,834,377 | A | 9/1974 | Lebold |
| 3,848,286 | A | 11/1974 | Kahmann |
| 3,859,991 | A | 1/1975 | Theodores |
| 3,916,886 | A | 11/1975 | Rogers |
| 3,986,501 | A | 10/1976 | Schad |
| 4,289,122 | A | 9/1981 | Mason et al. |
| 4,329,982 | A | 5/1982 | Heaney |
| 4,446,856 | A | 5/1984 | Jordan |
| 4,459,980 | A | 7/1984 | Perser et al. |
| 4,550,721 | A | 11/1985 | Michel |
| 4,554,912 | A | 11/1985 | Haberman |
| 4,556,054 | A | 12/1985 | Paulseth |
| 4,559,934 | A | 12/1985 | Philipp |
| 4,566,447 | A | 1/1986 | Deis |
| 4,646,726 | A | 3/1987 | Westin et al. |
| 4,649,939 | A | 3/1987 | Curtis |
| 4,651,723 | A | 3/1987 | Satoh |
| 4,676,801 | A | 6/1987 | Lundeen |
| 4,817,589 | A | 4/1989 | Wertz |
| 5,020,523 | A | 6/1991 | Bodine |
| 5,088,479 | A | 2/1992 | Detoro |
| 5,088,480 | A | 2/1992 | Wang |
| 5,219,324 | A | 6/1993 | Hall |
| 5,224,925 | A | 7/1993 | Varn |
| 5,257,969 | A | 11/1993 | Mance |
| 5,277,699 | A | 1/1994 | Williamson |
| D350,204 | S | 8/1994 | Mance |
| 5,370,604 | A | 12/1994 | Bernardoni |
| 5,376,068 | A | 12/1994 | Grifka |
| 5,382,224 | A * | 1/1995 | Spangler .................. 602/23 |
| 5,429,588 | A | 7/1995 | Young et al. |
| 5,542,912 | A | 8/1996 | Hess |
| 5,569,174 | A | 10/1996 | Varn |
| 5,700,237 | A | 12/1997 | Hess |
| 5,817,041 | A | 10/1998 | Bader |
| 5,830,166 | A | 11/1998 | Klopf |
| 5,833,640 | A | 11/1998 | Vazquez, Jr. et al. |
| 5,843,010 | A | 12/1998 | Bodmer |
| 5,860,423 | A | 1/1999 | Thompson |
| 5,897,515 | A | 4/1999 | Willner et al. |
| D411,302 | S | 6/1999 | Rowell |
| 5,961,477 | A | 10/1999 | Turtzo |
| 6,102,881 | A | 8/2000 | Quackenbush et al. |
| D431,296 | S | 9/2000 | Swedberg et al. |
| 6,206,807 | B1 | 3/2001 | Cowans et al. |
| 6,230,726 | B1 | 5/2001 | Dell |
| 6,267,357 | B1 | 7/2001 | Ebey et al. |
| 6,299,587 | B1 | 10/2001 | Birmingham |
| 6,361,517 | B1 | 3/2002 | Slinger |
| 6,409,692 | B1 | 6/2002 | Covey |
| 6,457,332 | B1 | 10/2002 | Schiavello |
| 6,602,217 | B2 | 8/2003 | Crawford et al. |
| 6,676,618 | B2 | 1/2004 | Andersen |
| 6,695,797 | B2 | 2/2004 | Trieloff |
| 6,793,640 | B1 | 9/2004 | Avon |
| D501,928 | S | 2/2005 | Smits |
| D503,480 | S | 3/2005 | Ingimundarson et al. |
| 6,860,864 | B2 | 3/2005 | Meyer |
| 6,926,687 | B2 | 8/2005 | Shields |
| 6,945,947 | B2 | 9/2005 | Ingimundarson et al. |
| D514,225 | S | 1/2006 | Sassi |
| 6,997,891 | B1 | 2/2006 | Vecsey |
| 7,018,352 | B2 * | 3/2006 | Pressman et al. ............... 602/27 |
| 7,112,180 | B2 | 9/2006 | Guenther |
| 7,125,392 | B2 | 10/2006 | Scott |
| 7,219,450 | B2 | 5/2007 | Langley |
| 7,294,114 | B1 | 11/2007 | Clement et al. |
| 7,458,950 | B1 * | 12/2008 | Ivany ............................. 602/27 |
| 2002/0077576 | A1 | 6/2002 | Saraceni |
| 2002/0129821 | A1 | 9/2002 | Trieloff |
| 2003/0073938 | A1 | 4/2003 | Crawford et al. |
| 2005/0038365 | A1 | 2/2005 | Scott |
| 2005/0070833 | A1 | 3/2005 | Shields |
| 2005/0070834 | A1 | 3/2005 | Herr et al. |
| 2005/0126047 | A1 * | 6/2005 | Kruijsen ..................... 36/118.5 |
| 2005/0234378 | A1 | 10/2005 | Ingimundarson et al. |
| 2006/0025712 | A1 | 2/2006 | Kammerer |
| 2006/0076706 | A1 | 4/2006 | Buethorn |
| 2006/0093703 | A1 | 5/2006 | Tooman |
| 2006/0270958 | A1 | 11/2006 | George |
| 2007/0010773 | A1 | 1/2007 | Watts |
| 2007/0038169 | A1 | 2/2007 | Alon et al. |
| 2007/0100268 | A1 | 5/2007 | Fisher |
| 2007/0191748 | A1 | 8/2007 | Buethorn |
| 2008/0077066 | A1 | 3/2008 | Lewis |
| 2008/0154167 | A1 | 6/2008 | Fisher |
| 2008/0171956 | A1 | 7/2008 | Jacobsen et al. |
| 2008/0196273 | A1 | 8/2008 | Kosta |
| 2008/0243042 | A1 | 10/2008 | Balzer |
| 2008/0300525 | A1 | 12/2008 | Shlomovitz |
| 2008/0312571 | A1 | 12/2008 | Waller |
| 2009/0105624 | A1 | 4/2009 | Warner |

* cited by examiner

ORTHOTIC FOOT BRACE

TECHNICAL FIELD OF THE INVENTION

The technical field relates to orthotics and, more particularly, to an orthosis for remediation of foot drop symptoms.

BACKGROUND

Foot drop, drop foot, and foot dangle are terms which have been employed to describe ankle and toe dorsiflexor paresis resulting in the inability to raise the foot at the ankle, such that the foot inclines towards and scrapes the ground when walking. Dorsiflexion is the motion the ankle joint makes when the foot points upward. This motion needs to occur when the foot comes off the ground so that the toes do not drag.

Foot drop makes walking difficult as the toes tend to drag on the ground which leads to tripping and instability. Patients adapt to this by using their hip muscles to exaggerate lifting the foot above the ground (known as a "steppage gait") or by swinging their leg outward so that the foot can clear the ground (known as "circumduction").

A common remediation technique for foot drop involved the employment of an ankle foot orthosis, or brace. The goal of bracing is to provide patients with a more normal and comfortable gait. These devices often require professional fitting, which may imply taking of impressions of the affected foot, and customized shoes. Significant delays can occur between the fitting and receipt of the customized orthosis.

Several braces have been developed for foot drop. Short leg fixed braces, for instance U.S. Pat. No. 5,429,588, fit into the footwear, do not flex at ankle joint, and do not allow plantar flexion nor dorsiflexion, i.e. they do not provide quite as natural of a gait. Dorsiflexion assist short leg braces are similar to short leg fixed braces but with a spring-like hinge that acts to raise the foot, i.e. dorsiflex the ankle when the foot comes off of the ground. It offers the advantage of a more normal gait pattern. Solid ankle braces, with or without posterior stop, also fit inside the footwear and have a hinge that allows normal dorsiflexion. They can or cannot allow plantarflexion, i.e. it can or cannot let the foot point downward. Energy return braces also fit inside the footwear and use a natural flex built into the material of the brace to provide assist in dorsiflexion. These braces are often made of polymers or carbon graphite materials.

BRIEF SUMMARY OF THE INVENTION

It is therefore an aim of the present invention to address the above mentioned issues.

According to a general aspect, there is provided an orthotic foot brace for a person wearing a footwear. The orthotic foot brace comprises: a lower leg holder securable around a lower leg of the person; a lower leg strut secured to the lower leg holder and extending downwardly towards the footwear; a foot strut having a rear section secured to the vertical strut, at least one of a median section and a lateral section located on a respective side of the footwear and extending outwardly thereof, and a front section securable to an instep section of the footwear; and at least one brace retaining member secured to the foot strut juxtaposed to the footwear, and having at least a section extending on the median side of the footwear and having at least a section extending on the lateral side of the footwear, outwardly thereof, and restraining a rearwardly oriented pivotal movement of the brace.

According to another general aspect, there is provided an orthotic foot brace for a person wearing a footwear comprising: a frame including a lower leg holder securable to a lower leg of the person; a vertical section secured to the lower leg holder and extending downwardly towards the footwear; a foot section secured to the vertical section, extending outwardly of the footwear and forwardly towards an instep section of the footwear and securable to the instep section of the footwear; and a brace retaining member secured to the foot section, extending from a median side of the footwear to a lateral side of the footwear, and restraining a rearwardly oriented pivotal movement of the brace.

BRIEF DESCRIPTION OF THE DRAWINGS

It will be noted that throughout the appended drawings, like features are identified by like reference numerals.

DETAILED DESCRIPTION

Figure 1:
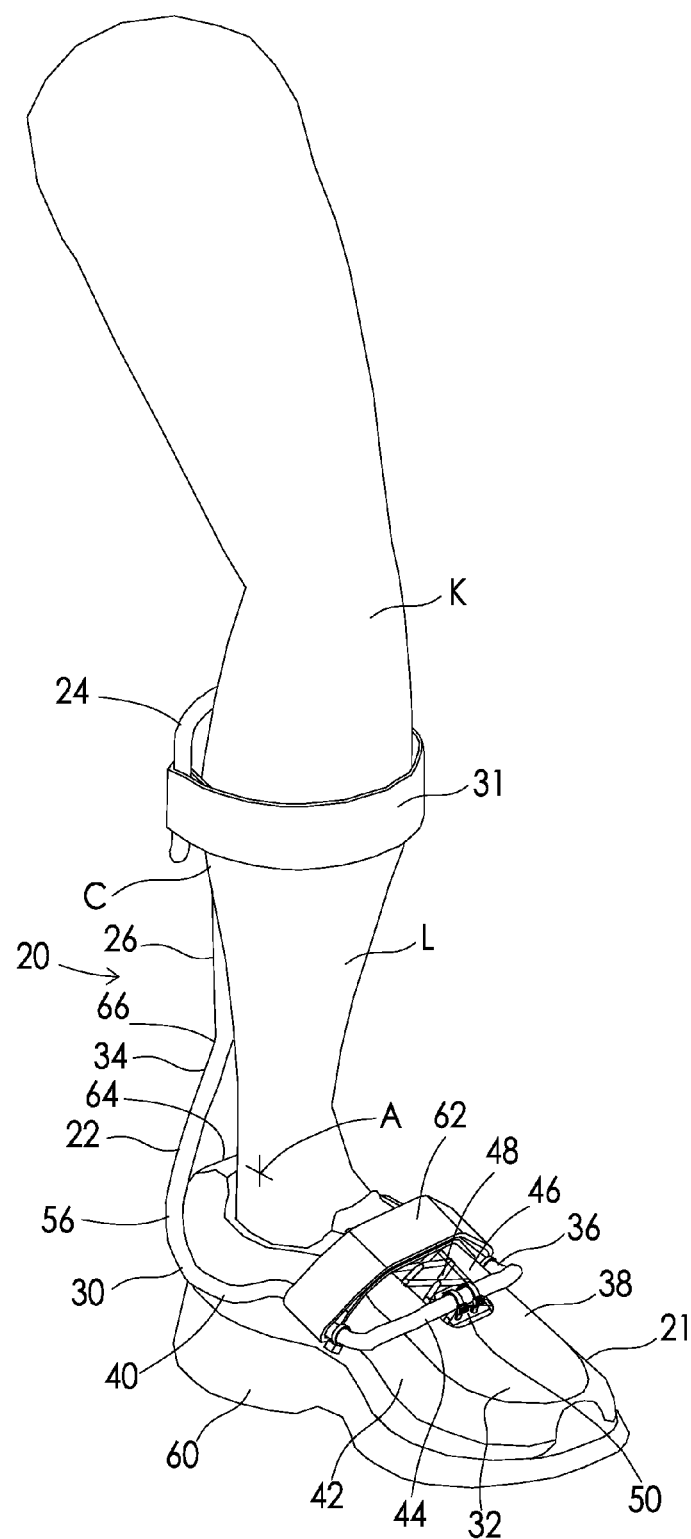
FIG. 1 is a front perspective view of an orthotic foot brace in accordance with a first embodiment, wherein the brace is secured to a person's lower leg and footwear.
Figure 2:
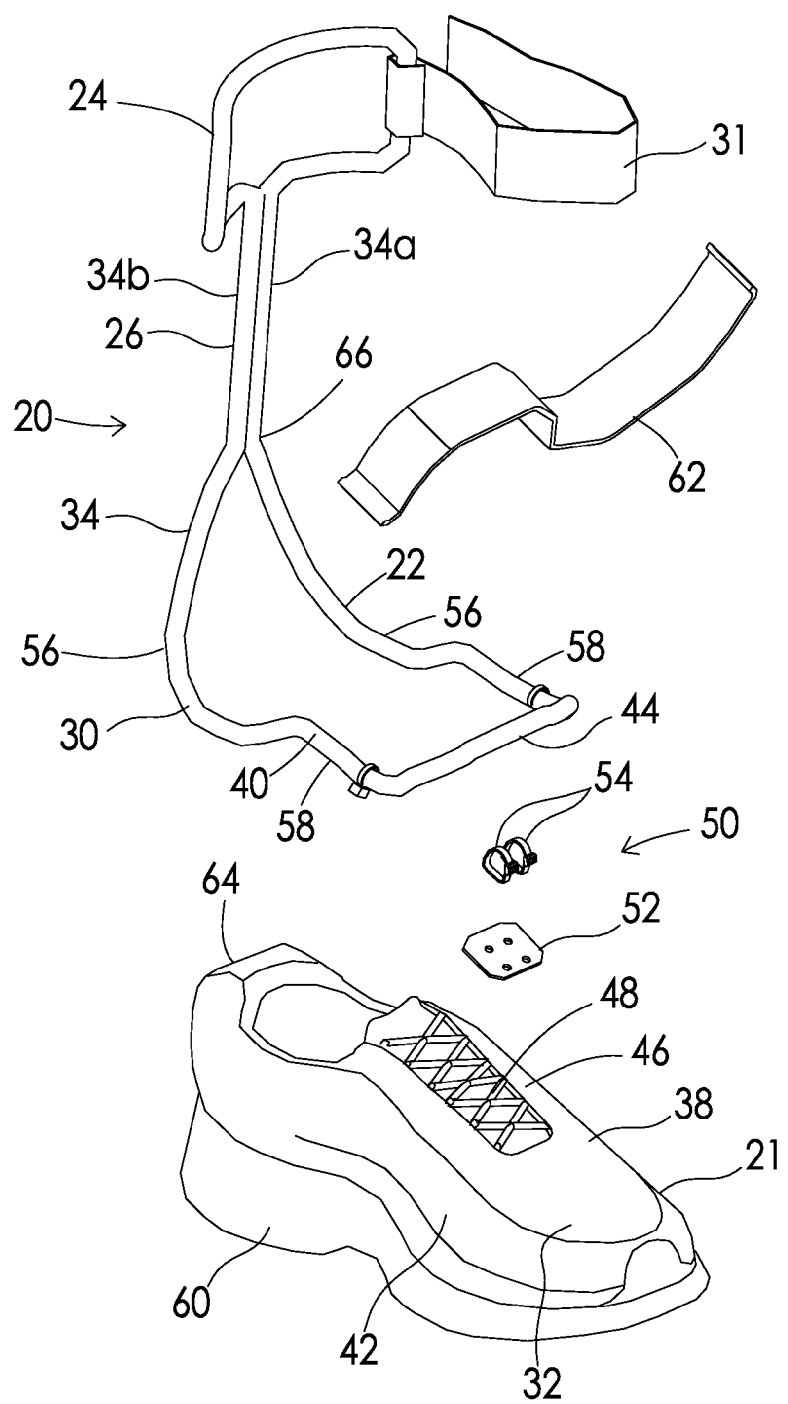
FIG. 2 is a front perspective view, exploded, of the orthotic foot brace and footwear shown in FIG. 1.
Figure 3:
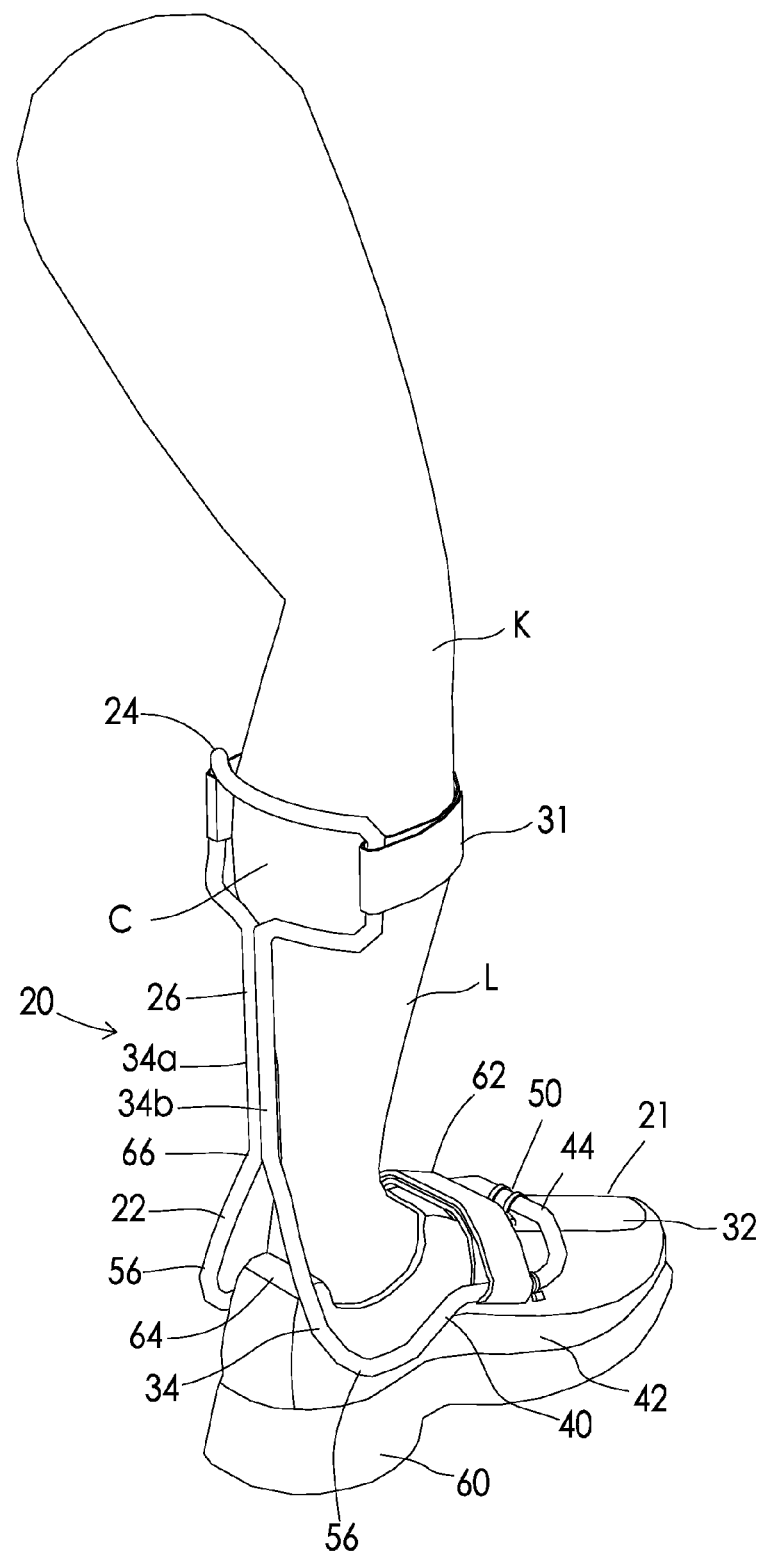
FIG. 3 is a rear perspective view of the orthotic foot brace shown in FIG. 1, wherein the brace is secured to the person's lower leg and footwear.

Referring to FIGS. 1 to 3, there is shown an orthotic foot brace 20, also referred to ankle-foot orthoses, in accordance with a first embodiment. The foot brace 20 is securable to a person's lower leg L and footwear (or shoe) 21 and encompasses an ankle joint A. It is intended to control position and motion of the person's ankle to compensate for weakness. For conciseness, only the left foot brace which is securable to the person's left lower leg is shown and described below. For this embodiment, the right foot brace is similar or can include only minor modifications.

The brace 20 has a structural frame 22 including a lower leg holder 24 securable to the person's lower leg L, below the knee K, a lower leg vertical section 26 or strut extending from the lower leg holder 24 towards the footwear 21, and a foot section 30 or strut extending from the vertical section 26 towards a toe section 32 of the footwear 21 and securable to the footwear 21, outwardly thereof.

In the embodiment shown, the lower leg holder 24 is a calf cuff juxtaposed to the person's calf C, rearwardly of the person's calf C. More particularly, the calf cuff 24 is designed to abut the upper part of the calf C, below the knee K. A leg attachment strap 31 is secured to one vertical part of the calf cuff 24 and is designed to connect the opposed vertical part of the calf cuff 24 by extending toward the front of the tibia and thereby encircling the person's lower leg L and securing the upper part of the brace 20 thereto. It is appreciated that, in alternative embodiments, the lower leg holder 24 can be positioned at different locations, anywhere above the ankle, below the knee K, and around the lower leg L. For instance and without being limitative, it can be juxtaposed to the person's tibia. It secures the brace 20 to the person's lower leg L. Moreover, it can have a different shape than the one shown in FIGS. 1 to 3.

In the embodiment shown, the brace 20 includes a single and continuous frame member 34 extending between the lower leg holder 24, the vertical section 26, and the foot section 30. The frame member 34 includes two frame member sections 34a, 34b juxtaposed in the vertical section 26 and spaced-apart in the lower leg holder 24 and foot section 30. In the embodiment shown, the frame member 34 is a rod with a circular cross-section. However, it is appreciated that it can be a substantially flat member or have any other appropriate shape.

The vertical section 26 extends rearwardly of the person's lower leg L, from the lower leg holder 24 to the foot section 30. It is appreciated that, in alternative embodiments (not shown), it can extend downwardly anywhere around the person's lower leg L. Furthermore, in the embodiment shown, the vertical section 26 has a substantially straight shape. However, in alternative embodiments, it can have a curved or any other appropriate shape. Furthermore, in an alternative embodiment (not shown), the frame member sections 34a, 34b can be spaced-apart from one another either entirely along their length or only along a section thereof. For instance and without being limitative, the frame member sections 34a, 34b can extend downwardly on opposed sides of the lower leg, spaced-apart from one another.

The foot section 30 can be divided into a lateral section 36 which is juxtaposed to a lateral side 38 of the footwear 21, i.e. the outside part of the footwear 21, a median section 40 which is juxtaposed to a median side 42 of the footwear 21, i.e. the inside part of the footwear 21, and a front section 44 which extends above an instep section 46 of the footwear 21, i.e. the part located on the top of the foot, and forwardly of an inner space opening. The frame member 34 extends continuously between each section 36, 40, 44 and is located outwardly of the footwear 21, i.e. it is juxtaposed to the outer surface of the footwear 21.

The brace 20 is secured to the footwear 21 in the front section 44. It is secured to the footwear laces 48 through attachment means 50 including a spreader plate 52 and two attachment members 54. The attachment members 54 attach the spreader plate 52 and the frame member 34 to the laces 48. More particularly, the attachment members 54 are inserted in apertures defined in the spreader plate 52 and surround the footwear laces 48 and the frame member 34. It is appreciated that the brace 20 can be secured to the footwear 21 by any other appropriate technique. For instance and without being limitative, the footwear laces 48 can surround the frame member 34 and fasten the latter. In alternative embodiments (not shown), it can be secured to other footwear components and the attachment means can be adapted in accordance with the footwear design.

In the lateral and median sections 36, 40, the frame member 34 has a substantially curved shaped section 56 to follow the footwear shape in a region corresponding to the person's ankle followed by a substantially straight section 58. The frame member 34 in the lateral and median sections 36, 40 extends longitudinally along the footwear 21, outwardly thereof, above the outsole 60.

A foot band 62 is mounted to the straight sections 58 of the lateral and median sections 36, 40. The foot band 62 encircles the frame member 34 in the lateral and median sections 36, 40 and creates an inwardly directed force. The foot band 62 extends over the instep section 46 of the footwear 21, behind the front section 44 of the frame member 34 and forwardly of the inner space opening. In the embodiment shown, the foot band 62 includes a pair of hook-and-loop type gripping elements, such as "VELCRO®", for securing sections of the foot band 62 together when engaged over the frame member 34 in the lateral and median sections 36, 40. Thus, the tension between the lateral and median sections 36, 40 is adjustable.

FIG. 3 shows that the frame member sections 34a, 34b are spaced apart above the binding 64 of the footwear 21, i.e. the higher edge of the footwear 21, to allow plantarflexion P, i.e. there is a space defined between the footwear binding 64 and a distal end 66 of the vertical section 26 which corresponds to the meeting point of both frame member sections 34a, 34b.

Figure 4:
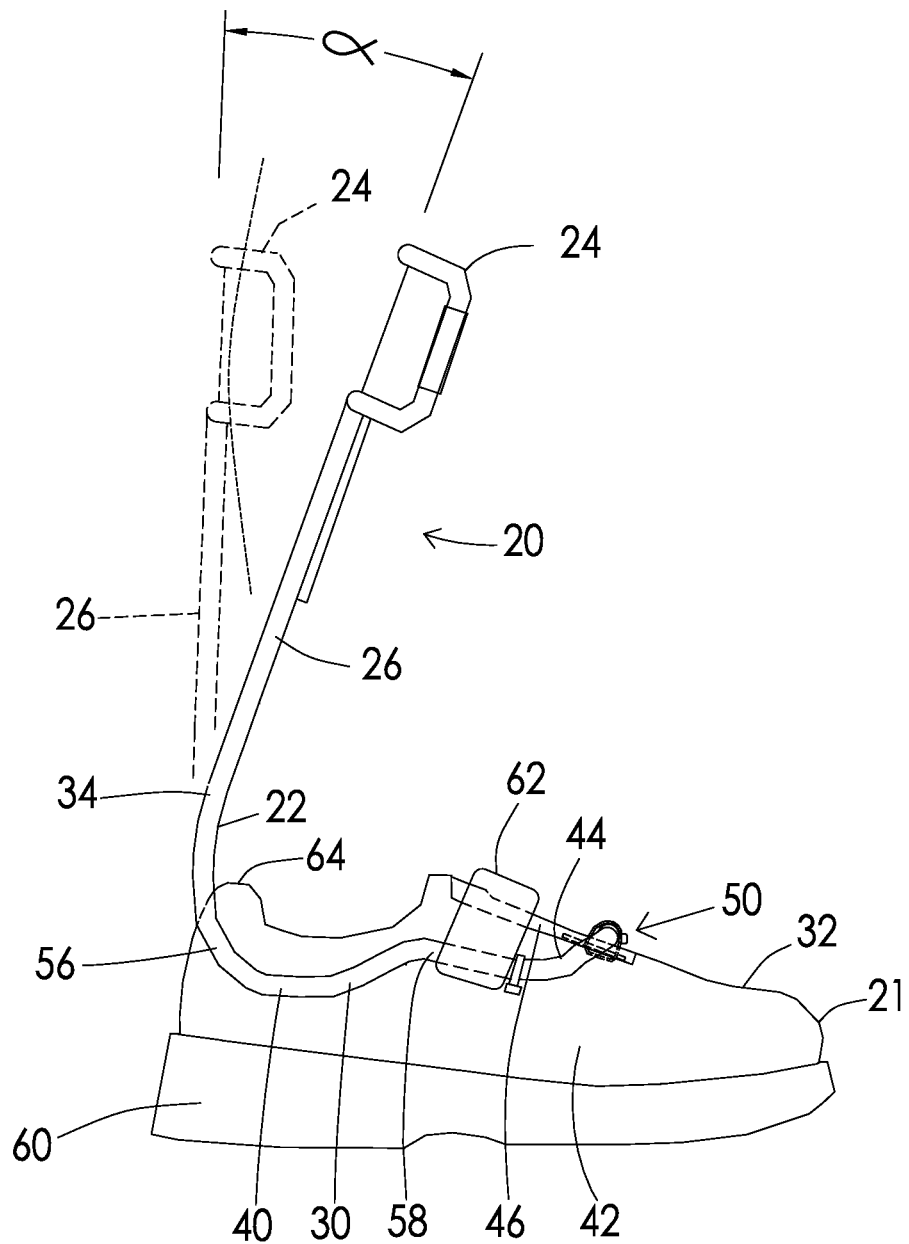
FIG. 4 is a side elevation view of the orthotic foot brace shown in FIG. 1, wherein the brace is secured to the footwear.

FIG. 4 shows the brace 20 secured to the footwear 21 but without being engaged with a person's lower leg L. The vertical section 26 of the brace 20 and the lower leg holder 24 extend forwardly towards the toe section 32 of the footwear 21. To attach the brace 20 to the lower leg L, the vertical section 26 is pulled rearwardly and, when attached, the lower leg holder 24 and the vertical section 26 apply a forwardly oriented pressure to the lower leg L. In a non-operative configuration, i.e. when detached from the lower leg L, the brace 20 defines an angle α with a vertical axis. The angle ranges between 10 and 30 degrees and, in an alternative embodiment, between 15 and 20 degrees. The compression stress applied to the person's lower leg L restricts the plantarflexion P of the foot and creates a bias for the dorsiflexion D of the foot.

Figure 5:
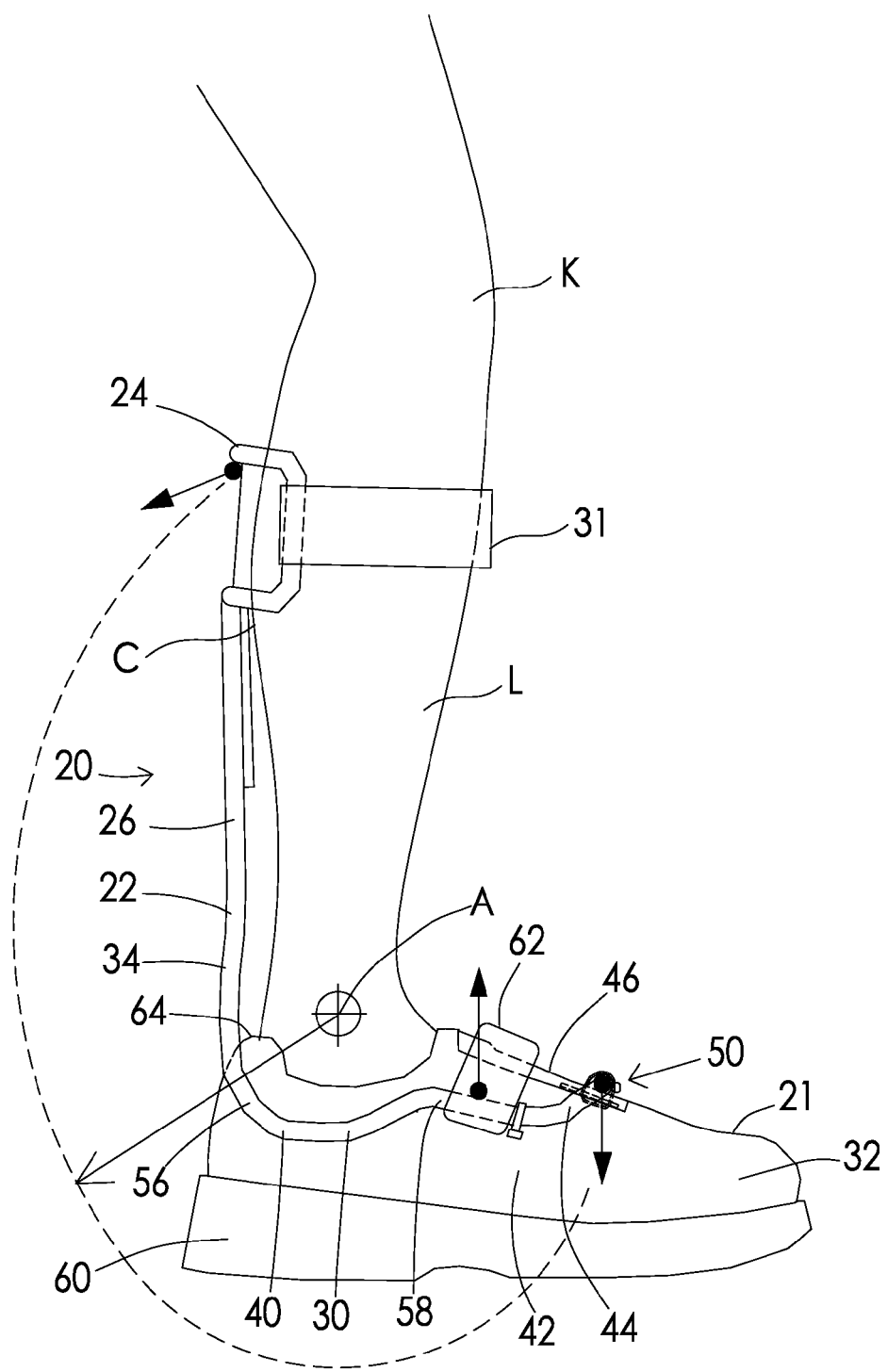
FIG. 5 is a side elevation view of the orthotic foot brace shown in FIG. 1, wherein the brace is secured to the person's lower leg and footwear.
Figure 6:
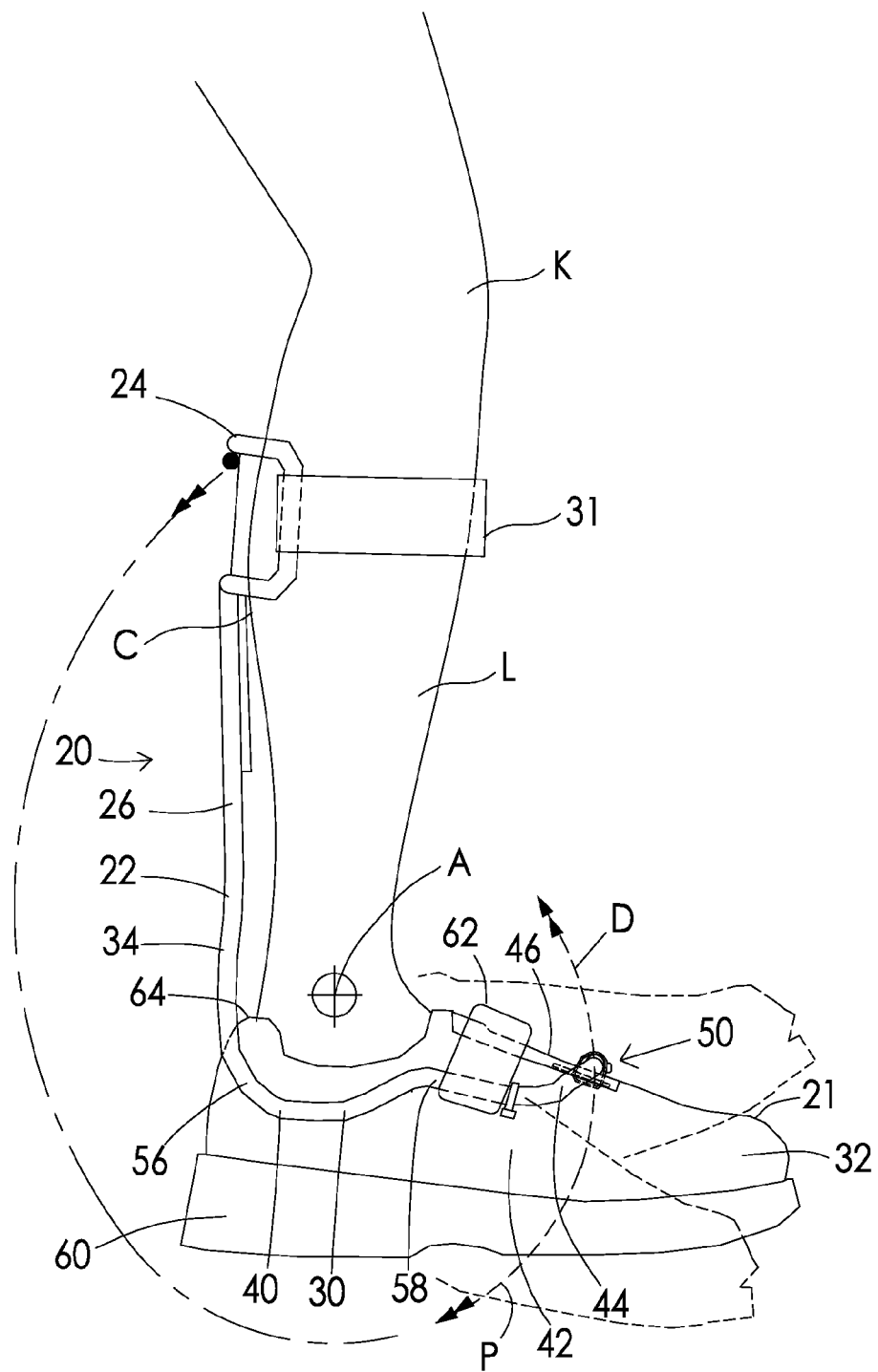
FIG. 6 is a side elevation view of the orthotic foot brace shown in FIG. 1, wherein the brace is secured to the person's leg and footwear and showing dorsiflexion and plantarflexion movements.

Referring to FIGS. 5 to 6, there is shown that during gaiting, the foot including the footwear 21 performs plantarflexions P and pivots about a pivoting axis which substantially corresponds to the ankle joint A. As a result, a tension force is applied on the foot band 62 when the foot performs plantarflexions P and the foot band 62 restricts the plantarflexion P of the foot, i.e. it creates a resistance to the plantarflexion moment P. A rearwardly extending tension is also applied on the lower leg holder 24. As mentioned above, the lower leg holder 24 applies a compression force on the lower leg L. Therefore, the combination of the tension applied to the foot band 62, the rearwardly extending tension, and the compression force applied on the lower leg L creates the resulting dorsiflexion moment D. The brace 20 conveys the foot including the footwear 21 to return to its normal, resting position.

The foot band 62 acts as a retaining member by restraining a rearwardly and downwardly oriented pivotal movement of the brace 20 and, more particularly, by restraining a downward movement of the lower leg holder 24, of the vertical section 26, and/or of the curved sections 56 during gaiting.

The same brace 20 can be used for either the left or the right foot.

Figure 7:
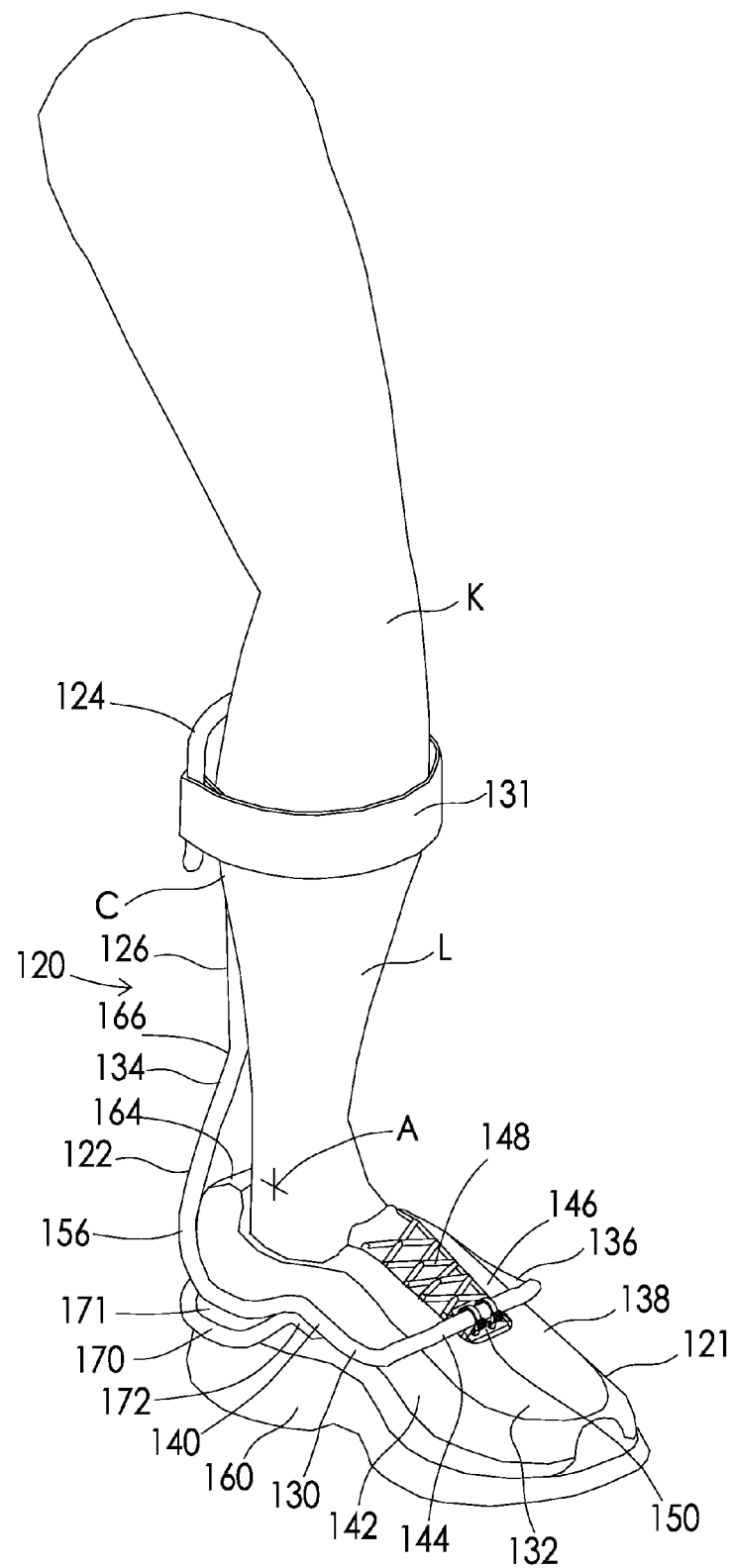
FIG. 7 is a front perspective view of an orthotic foot brace in accordance with a second embodiment, wherein the brace is secured to the person's leg and footwear.
Figure 8:
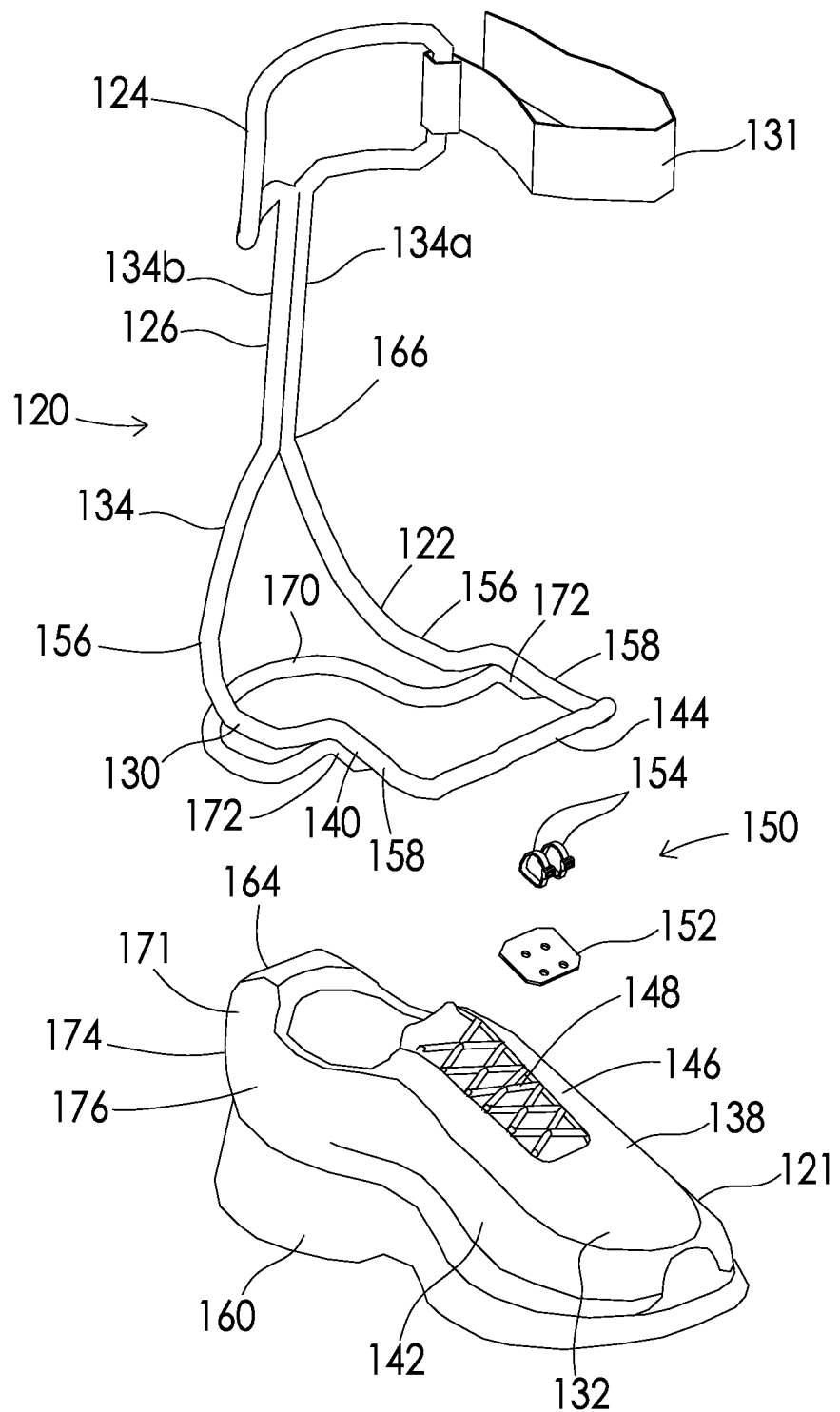
FIG. 8 is a front perspective view, exploded, of the orthotic foot brace and footwear shown in FIG. 7.
Figure 9:
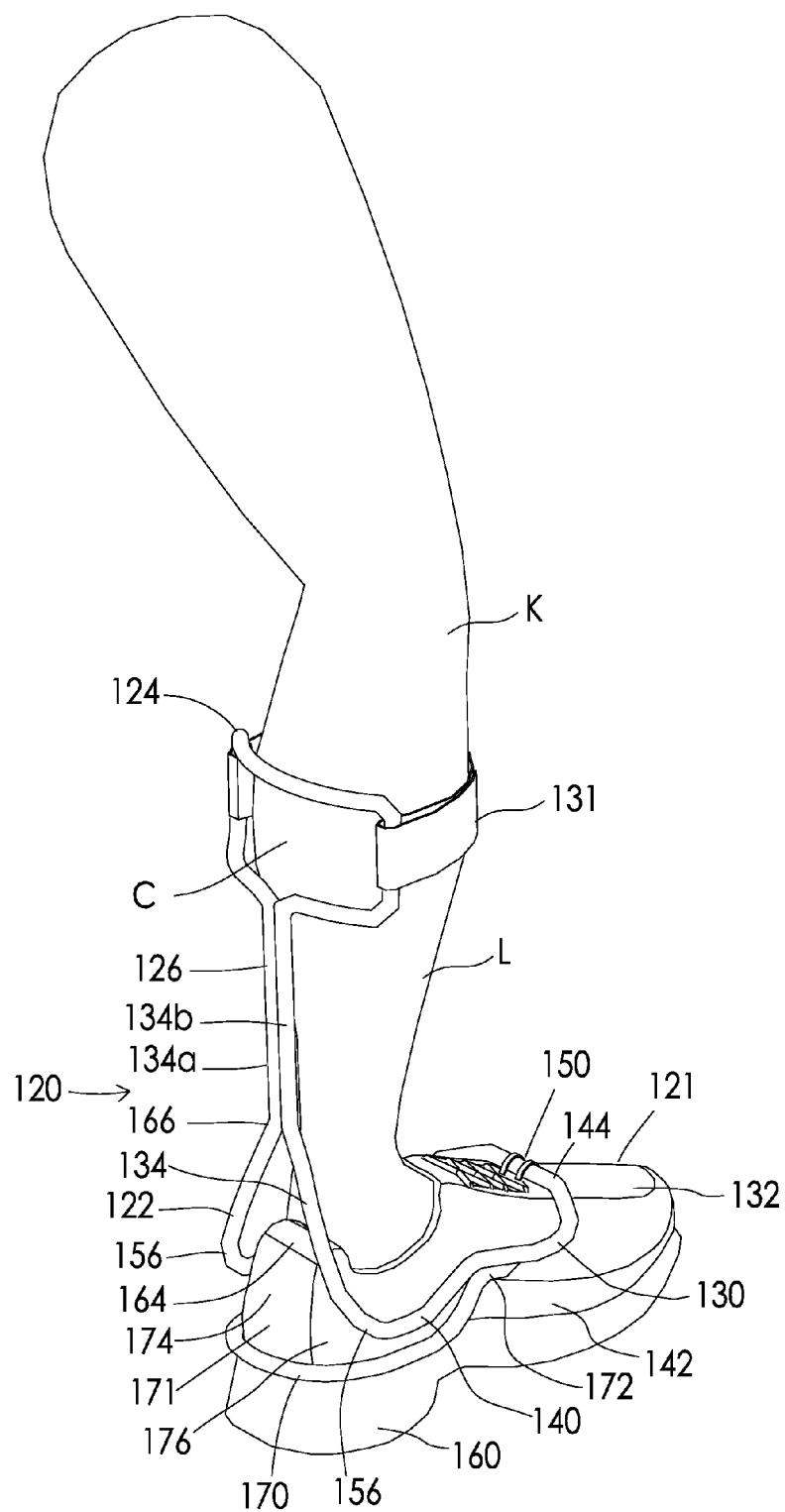
FIG. 9 is a rear perspective view of the orthotic foot brace shown in FIG. 7, wherein the brace is secured to the person's leg and footwear.

Referring now to FIGS. 7 to 9, there is shown another embodiment wherein the features are numbered with reference numerals in the 100 series which correspond to the reference numerals of the previous embodiment. As it will be described in more details below, the orthotic foot brace 120 has a frame 122 similar to the brace 20 shown in FIGS. 1 to 6. However, the foot band 62 of the brace 20 is replaced by a heel support 170 extending between the lateral and median sections 136, 140 of the frame 122 and behind the footwear heel 171. As for the above described embodiment, only the left foot brace which is securable to the person's left lower leg is shown and described below.

The lower leg holder 124 including the leg attachment strap 131 will not be described in details since they are similar to the ones described above in reference to FIGS. 1 to 6. Furthermore, the vertical and the foot sections 126, 130 of the frame 122 and the attachment means of the frame 122 to the footwear 121 will not be described in detail since they are also similar to the ones described above in reference to FIGS. 1 to 6. As for the above-described brace 20, the brace 120 is located entirely outside of the footwear 121.

The heel support 170 is part of the brace frame 122. It has two opposite ends 172 attached to the straight section 158 of the frame member 134 in the lateral and median sections 136, 140, close to the end of the curved shaped section 156. It extends rearwardly of the footwear 121, behind the heel section 171. It is located in the lower portion of the footwear heel 171 above the outsole 60 and in the lower section of the footwear counter 174, i.e. the reinforcement used to maintain the heel of the foot, if any. The heel support 170 applies a compression force on the footwear quarters 176. The compression force maintains the heel support 170 in contact with the footwear 121 and substantially prevents or reduces its displacement relatively to the footwear 121. Thus, the lateral and median portions of the heel support 170 are slightly pulled away to insert to footwear quarters 176 therebetween. When disengaged from the footwear 121, the spacing between the lateral and median portions of the heel support 170 is slightly narrower than the thickness of the footwear quarters 176 where the heel support 170 is engaged.

Figure 10:
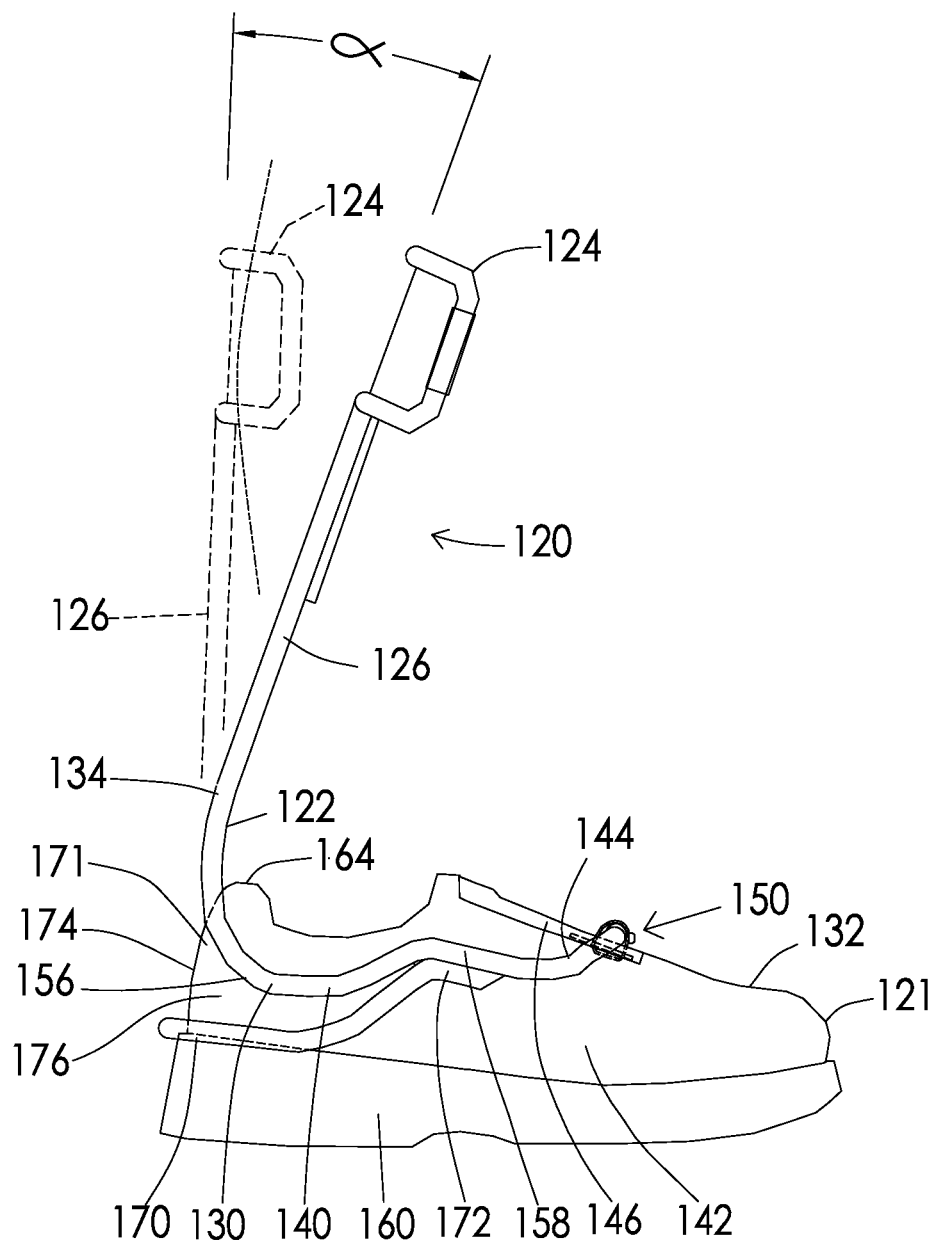
FIG. 10 is a side elevation view of the orthotic foot brace shown in FIG. 7, wherein the brace is secured to a footwear.
Figure 11:
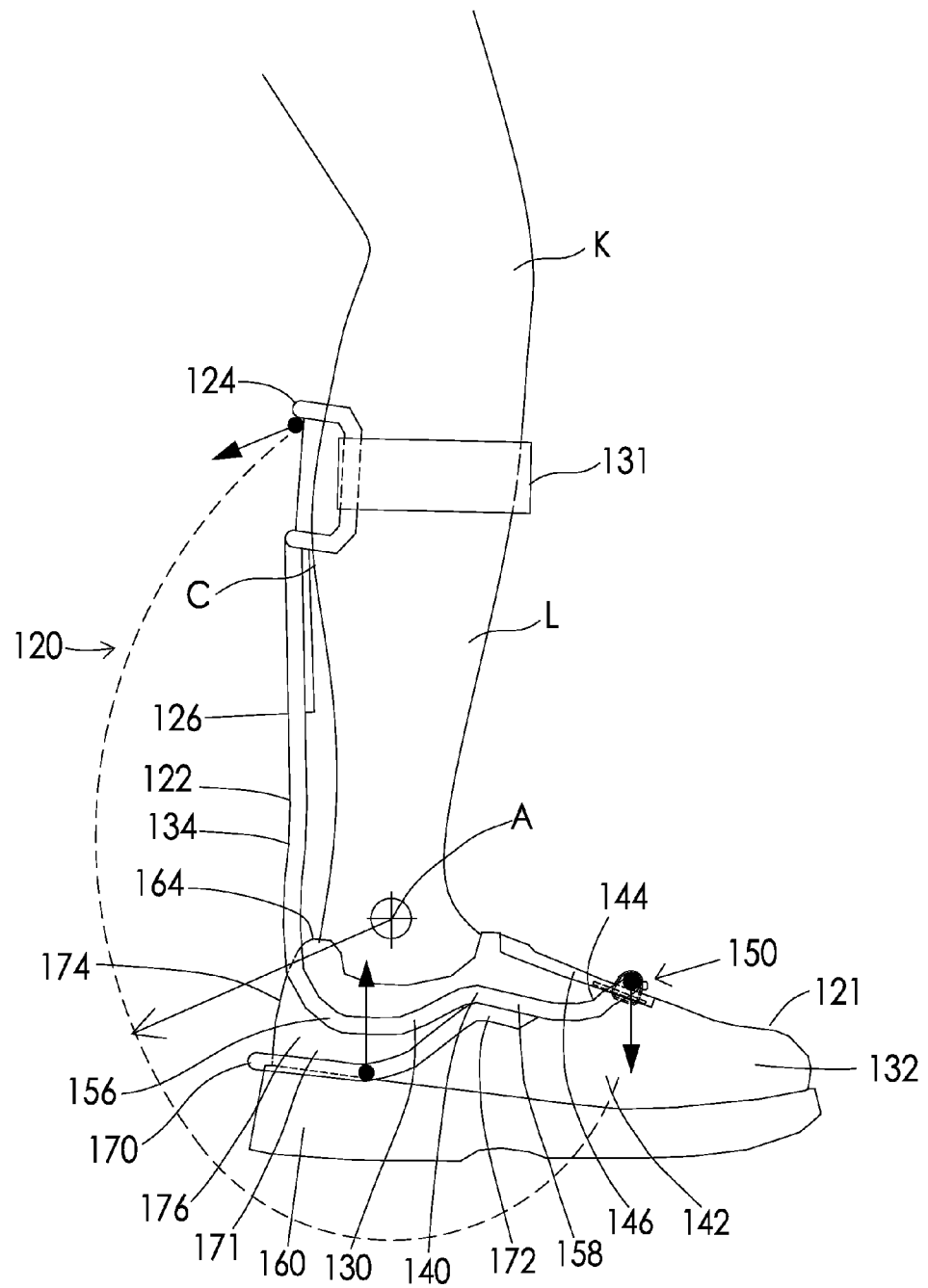
FIG. 11 is a side elevation view of the orthotic foot brace shown in FIG. 7, wherein the brace is secured to the person's leg and footwear.
Figure 12:
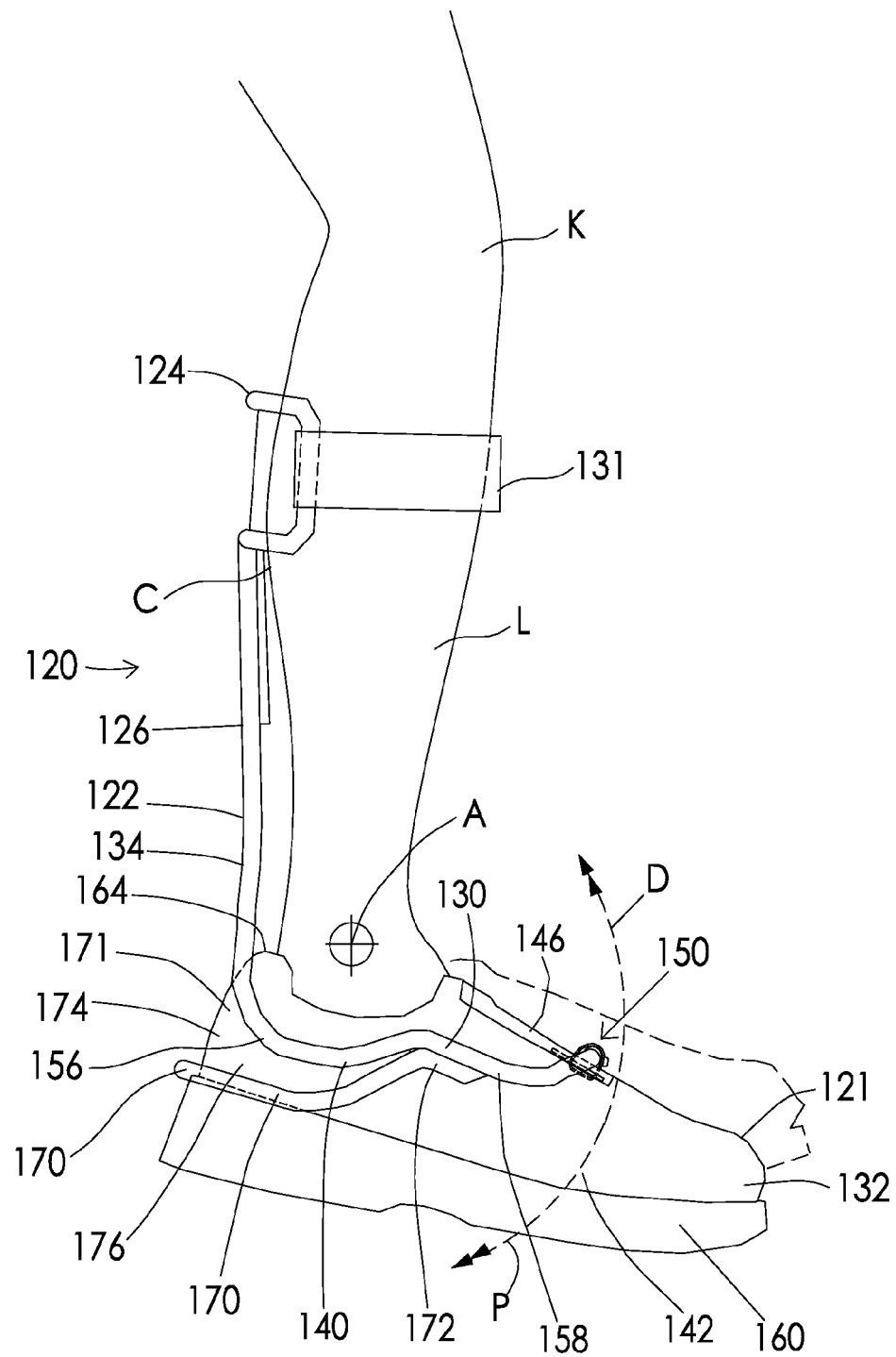
FIG. 12 is a side elevation view of the orthotic foot brace shown in FIG. 7, wherein the brace is secured to the person's leg and footwear showing dorsiflexion and plantarflexion movements.
Figure 13:
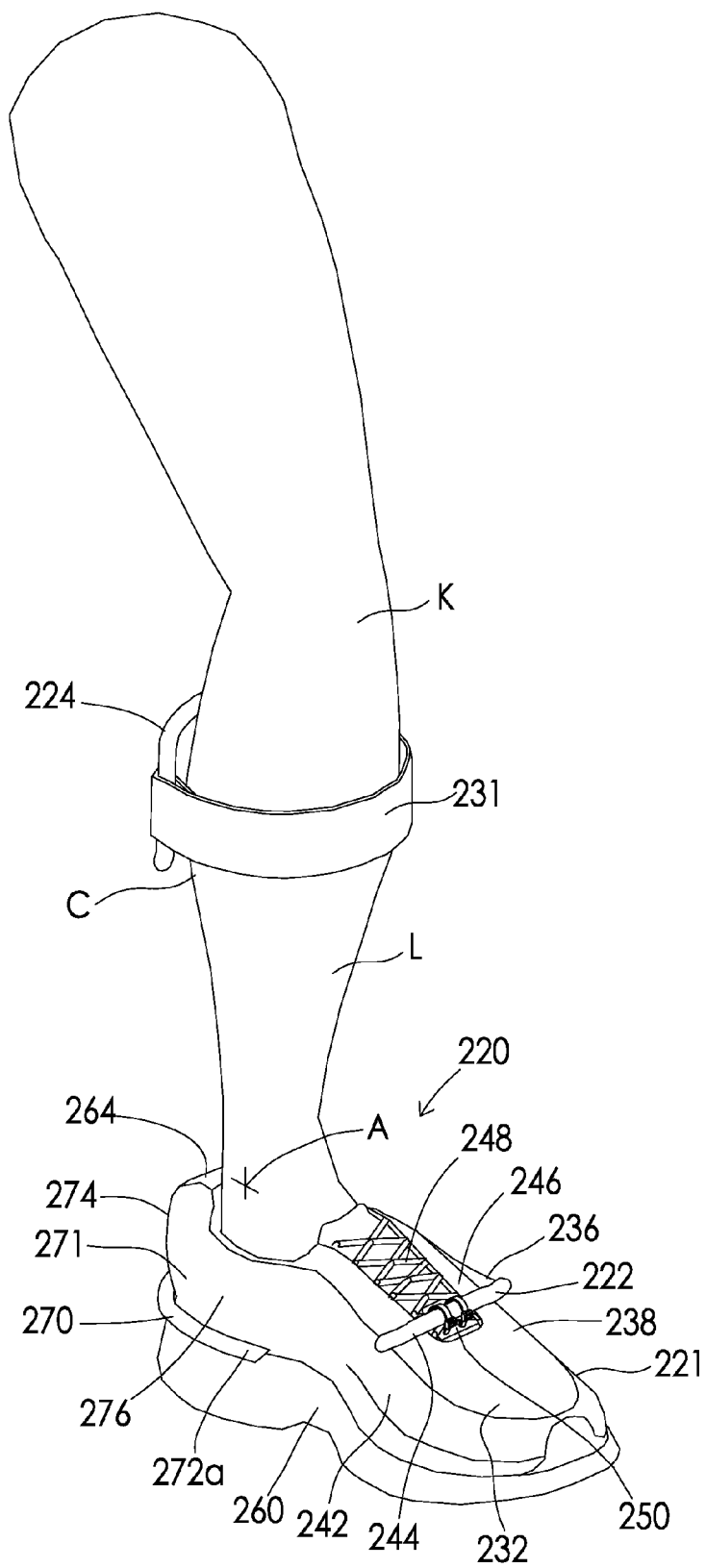
FIG. 13 is a front perspective view of an orthotic foot brace in accordance with a third embodiment, wherein the brace is secured to the person's leg and footwear.
Figure 14:
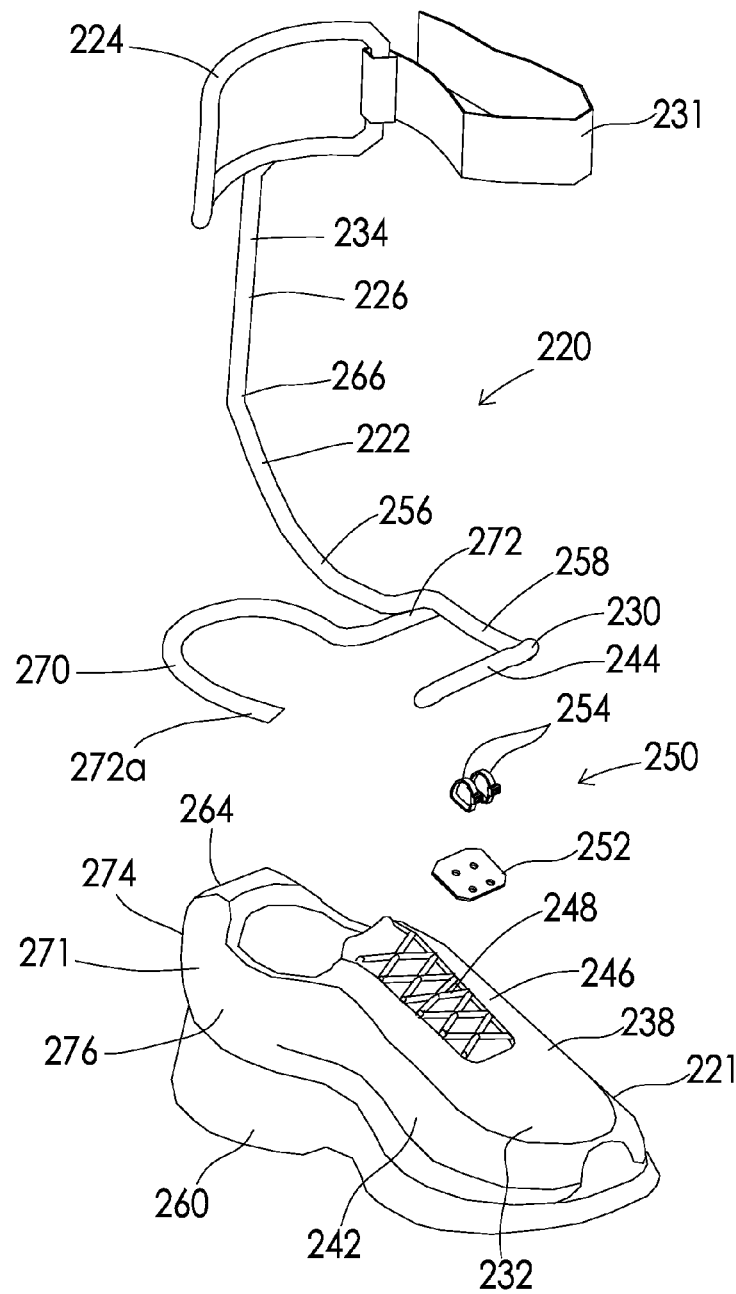
FIG. 14 is a front perspective view, exploded, of the orthotic foot brace and footwear shown in FIG. 13.

Referring now to FIGS. 10 to 12, there is shown that the heel support 170 can be attached to different sections of the brace frame 122. In FIGS. 10 and 11, sections of the heel support 170, close to the ends 172, are attached and juxtaposed to the straight section 158 of the frame member 134 in the lateral and median sections 136, 140. In FIG. 12, sections of the heel support 170, close to the ends 172, are attached and juxtaposed to the end of the curved shaped sections 156 in the lateral and median sections 136, 140. It is appreciated that, in alternative embodiments (not shown), the heel support 170 can be attached to different sections of the brace frame 122. For instance and without being limitative, the heel support 170 can be mounted anywhere along the lateral and median sections 136, 140.

FIG. 10 shows the brace 120 secured to the footwear 121 but without being engaged with a person's lower leg L. As for the above-described brace 20, the vertical strut 126 extends forwardly towards the toe section 132 of the footwear 121. To attach the brace 120 to the lower leg L, the vertical section 126 is pulled rearwardly and, when attached, the lower leg holder 124 and the vertical section 126 apply a forwardly oriented pressure, or a compression force on the lower leg L. In a non-operative configuration, i.e. when detached from the lower leg L, the brace 120 defines an angle ranging between 10 and 30 degrees and, in an alternative embodiment, between 15 and 20 degrees. As mentioned above, the compression stress applied to the person's lower leg L restricts the plantarflexion P of the foot and creates a bias for the dorsiflexion D of the foot.

Referring to FIGS. 11 and 12 and as mentioned above, there is shown that during gaiting, the foot including the footwear 121 performs plantarflexions P and pivots about a pivoting axis which substantially corresponds to the ankle joint A. As a result, an upwardly oriented force is applied on the heel support 170 when the foot performs plantarflexions P. Since the heel support 170 applies a compression force on the footwear quarters 176 which reduces displacement of the heel support 170 relatively to the footwear 121, the heel support 170 restricts the plantarflexion P of the foot, i.e. it creates a resistance to the plantarflexion moment P. A rearwardly extending tension is also applied on the lower leg holder 124. As mentioned above, the lower leg holder 124 applies a compression force on the lower leg L. Therefore, the combination of the upwardly oriented force on the heel support 170, the rearwardly extending tension and the natural compression force applied on the lower leg L creates the resulting dorsiflexion moment D. The brace 120 conveys the foot including the footwear 121 to return to its normal, resting position.

The heel support 170 acts as a retaining member by restraining a rearwardly and downwardly oriented pivotal movement of the brace 120 and, more particularly, by restraining a downward movement of the lower leg holder 124, of the vertical section 126, and/or of the curved sections 156 during gaiting.

As for the same brace 20, the brace 120 can be used for either the left or the right foot.

In alternative embodiments (not shown), the heel support can be divided in two spaced-apart sections extending rearwardly towards the footwear heel from the lateral and median sections 136, 140, without being connected to one another. Thus, each heel support sections have a rearwardly extending free end.

Referring now to FIGS. 13 to 17, there is shown another embodiment wherein the features are numbered with reference numerals in the 200 series which correspond to the reference numerals of the previous embodiments. As it will be described in more details below, the frame 222 of the orthotic foot brace 220 differs from the frames 22, 122 of braces 20 and 120 shown in FIGS. 1 to 12. The brace 220 does not include a foot band 62 but a heel support 270 extending between the lateral and median sections 236, 240 and behind the footwear heel 271. Furthermore, only one end of the heel support 270 is secured to the foot section 230 of the brace 220. For conciseness, only the left foot brace which is securable to the person's left lower leg is shown and described below. For this embodiment, the right foot brace is a mirror image thereof.

The lower leg holder 224 including the leg attachment strap 31 will not be described in detail since they are similar to the ones described above in reference to FIGS. 1 to 6. Furthermore, the attachment means of the frame 222 to the footwear 221 will not be described in detail since they are also similar to the ones described above in reference to FIGS. 1 to 6. As for the above-described braces 20, 120, the brace 220 is entirely located outside of the footwear 221, i.e. it is juxtaposed to an outer surface of the footwear 221.

Figure 15:
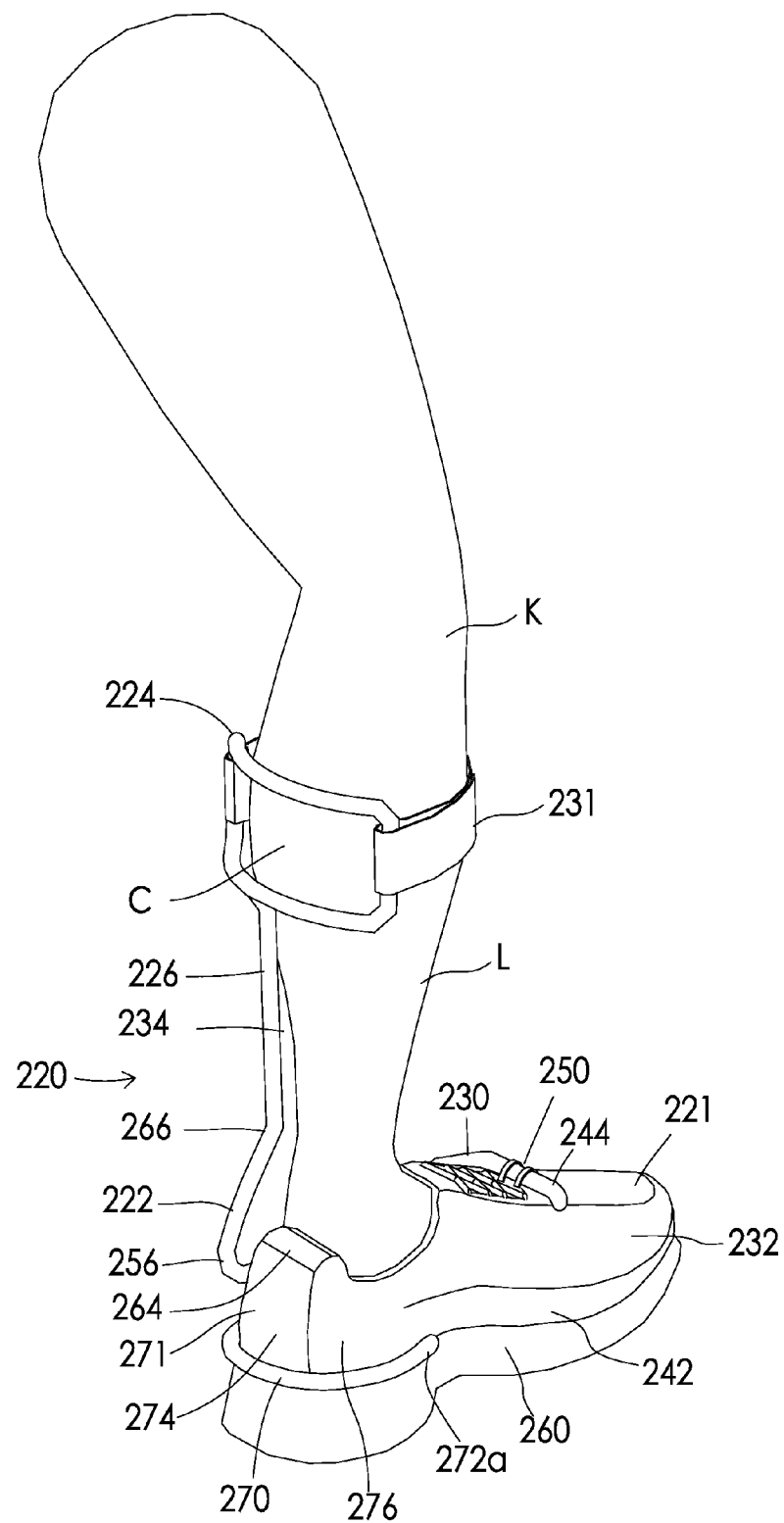
FIG. 15 is a rear perspective view of the orthotic foot brace shown in FIG. 13, wherein the brace is secured to the person's leg and footwear.

In the vertical section 226, a single rod, or frame member 234, extends downwardly from the lower leg holder 224 towards the foot section 230. On the opposite of the above-described braces 20, 120, the foot section 230 includes a frame member 234 extending continuously from the vertical section 226 to the front section 244 juxtaposed to the lateral side of the footwear 221. No frame member 234 extends continuously from the vertical section 226 to the front section 244 on the median side of the footwear 221. The junction between the distal end 266 of the vertical section 226 and the curved section 256 of the frame member 234 in the foot section 230 is located above the binding 264 of the footwear 221 to allow plantarflexion P, as shown in FIG. 15. The shape of the frame member 234 in the lateral section 236 and the front section 244 as well as the attachment means 250 to the footwear 221 in the front section 244 are similar to the ones of the above-described embodiments. Therefore, they will not be described in further detail.

The heel support 270 of the brace 220 has two opposite ends 272, the lateral end 272a is attached to the straight section 258 of the frame member 234 in the lateral section 236, close to the end of the curved shaped section 256. As for the embodiment described in reference to FIGS. 6 to 8, the heel support 270 can be attached to a different section of the brace frame 222. On the opposite of brace 120, the median end 272b of the heel support 270 is not attached to the median section 240, i.e. it is unattached. The median end 272b is juxtaposed to the median side 242 of the footwear 221 above the outsole 260, close to an inner arch of the footwear 221. The heel support 270 extends rearwardly of the footwear 221, behind the heel section 271. From the heel section 271 to the median section 240 of the footwear 221, the heel support 270 follows a junction of an upper end of the outsole 260 and a lower end of the footwear quarters 276.

It is appreciated that in an alternative embodiment (not shown), the heel support 270 can be attached to the median section 240 of the brace frame 222 and have an unattached (or free) lateral end 272a. Furthermore, as mentioned for the heel support 270, the heel support 270 can be attached to different sections of the brace frame 222.

As for the above-described heel support 270, the heel support 270 applies a compression force on the footwear quarters 276 which maintains the heel support 270 in contact with the footwear 221 and substantially prevents or reduces its displacement relatively to the footwear 221. The heel support 270 acts as a retaining member by restraining a rearwardly and downwardly oriented pivotal movement of the brace 220 and, more particularly, at restraining a downward movement of the lower leg holder 224, of the vertical section 226, and/or of the curved section 256 during gaiting.

As for the above-described embodiment, when disengaged from the lower leg L, the vertical strut 226 extends forwardly towards the toe section 232 of the footwear 221. Thus, a compression stress is applied to the person's lower leg L when engaged with the brace 220. The compression stress restricts the plantarflexion P of the foot and creates a bias for the dorsiflexion D of the foot.

Figure 16:
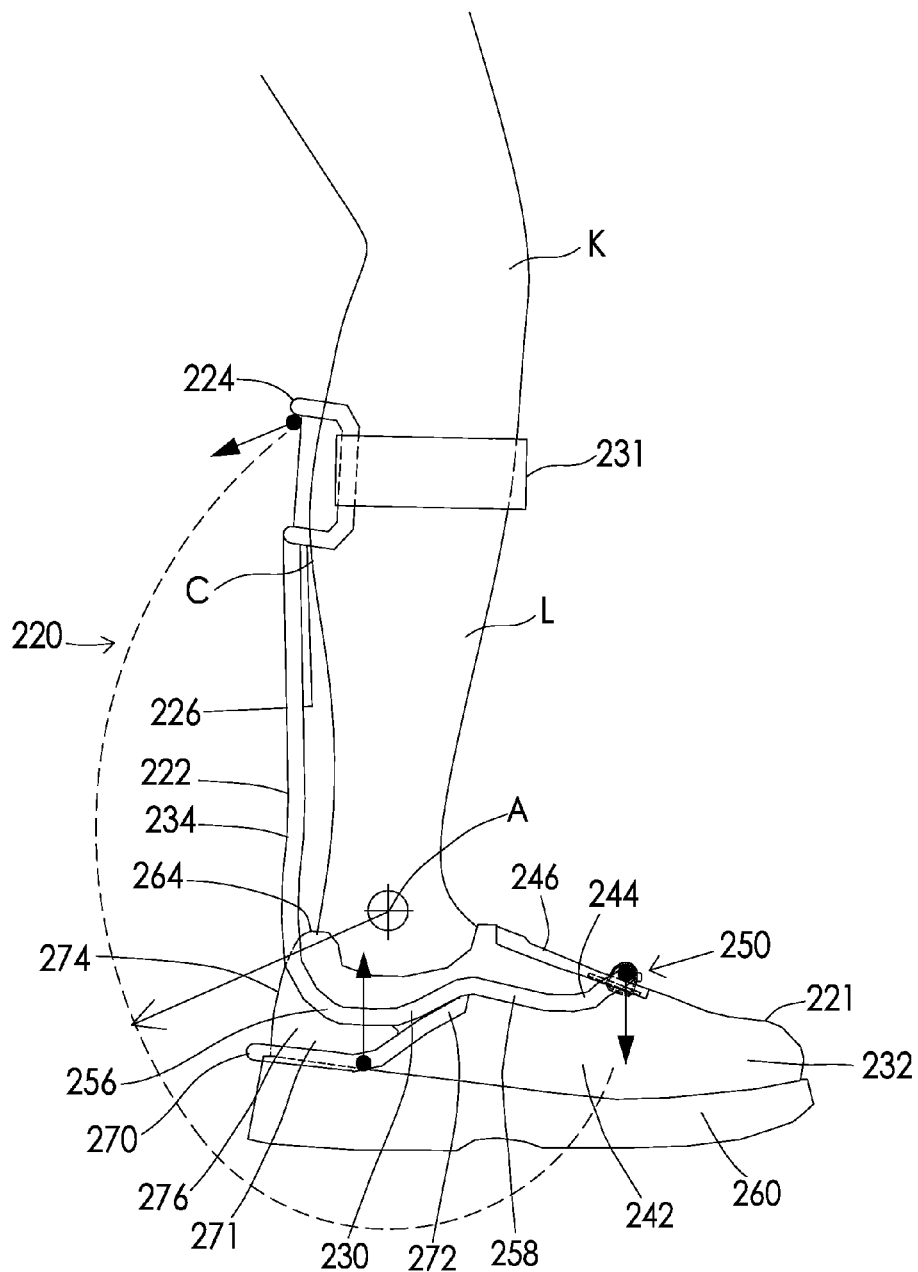
FIG. 16 is a side elevation view of the orthotic foot brace shown in FIG. 13, wherein the brace is secured to the person's leg and footwear.
Figure 17:
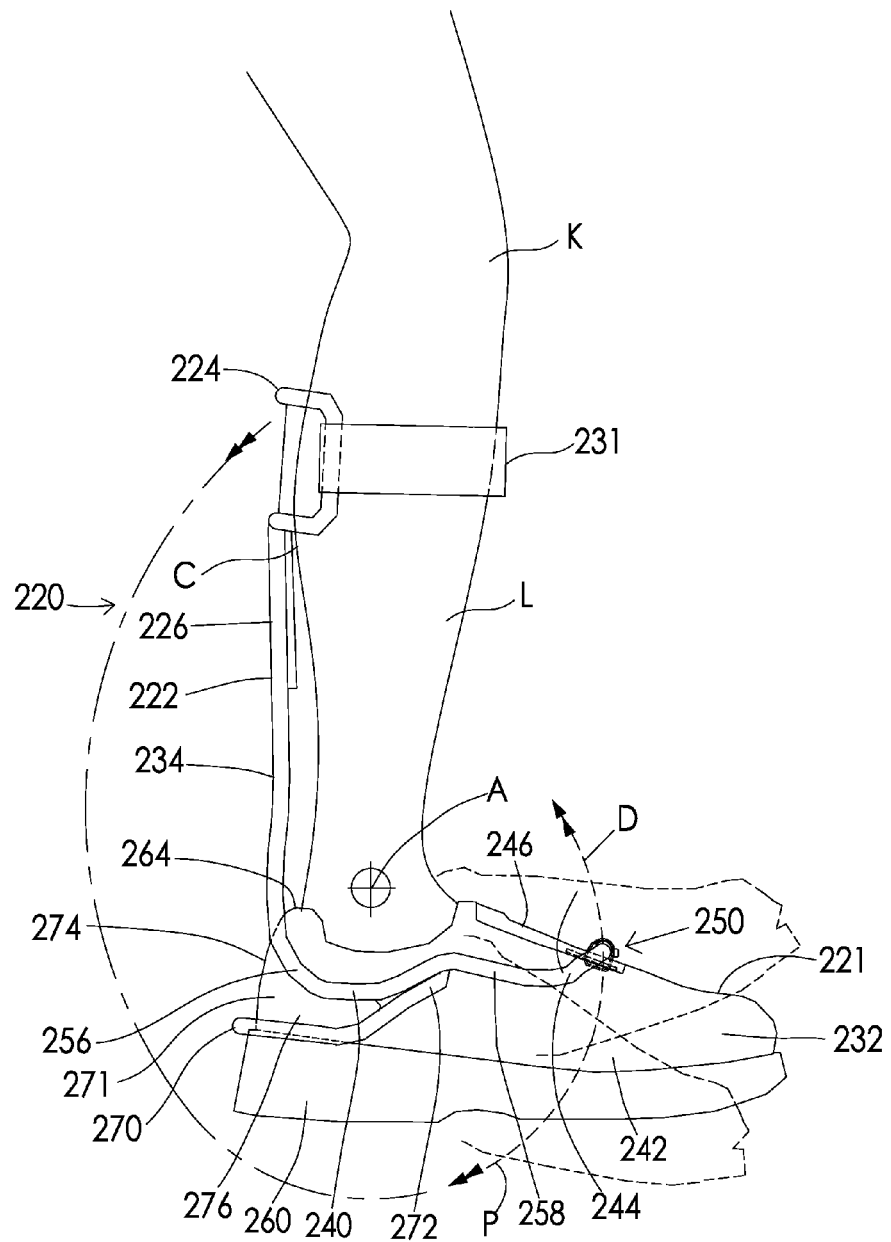
FIG. 17 is a side elevation view of the orthotic foot brace shown in FIG. 13, wherein the brace is secured to the person's leg and footwear and showing dorsiflexion and plantarflexion movements.
Figure 18:
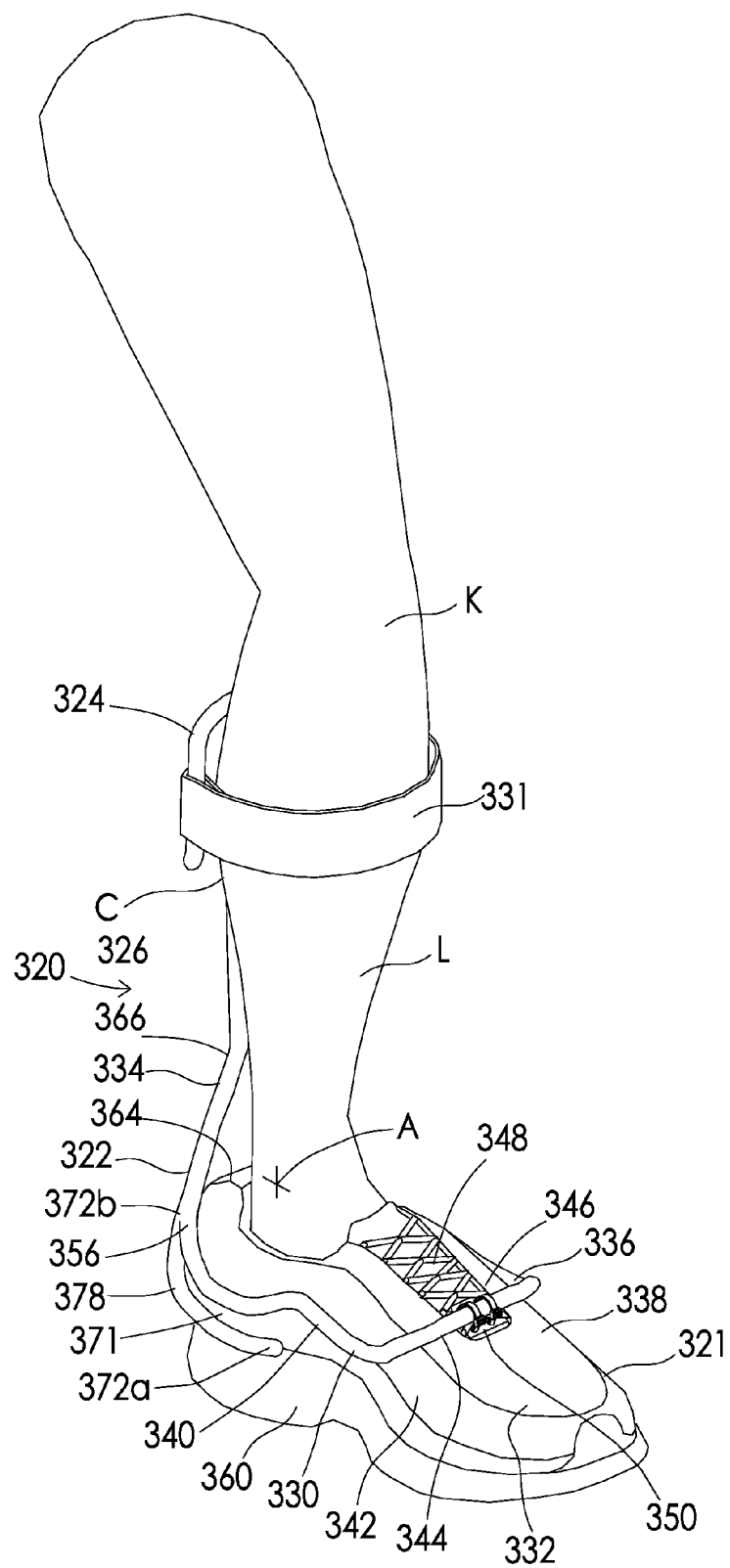
FIG. 18 is a front perspective view of an orthotic foot brace in accordance with a fourth embodiment, wherein the brace is secured to the person's leg and footwear.
Figure 19:
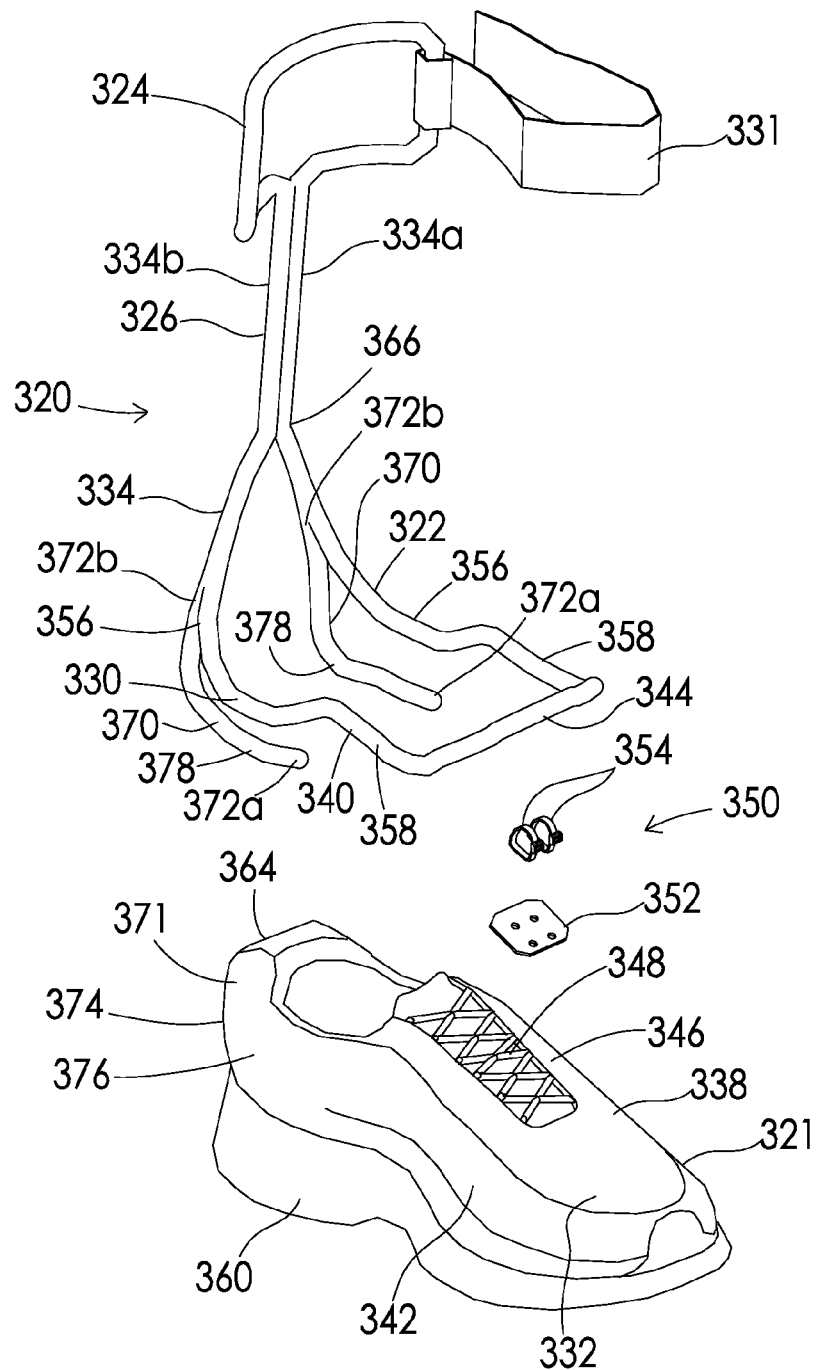
FIG. 19 is a front perspective view, exploded, of the orthotic foot brace and footwear shown in FIG. 18.
Figure 20:
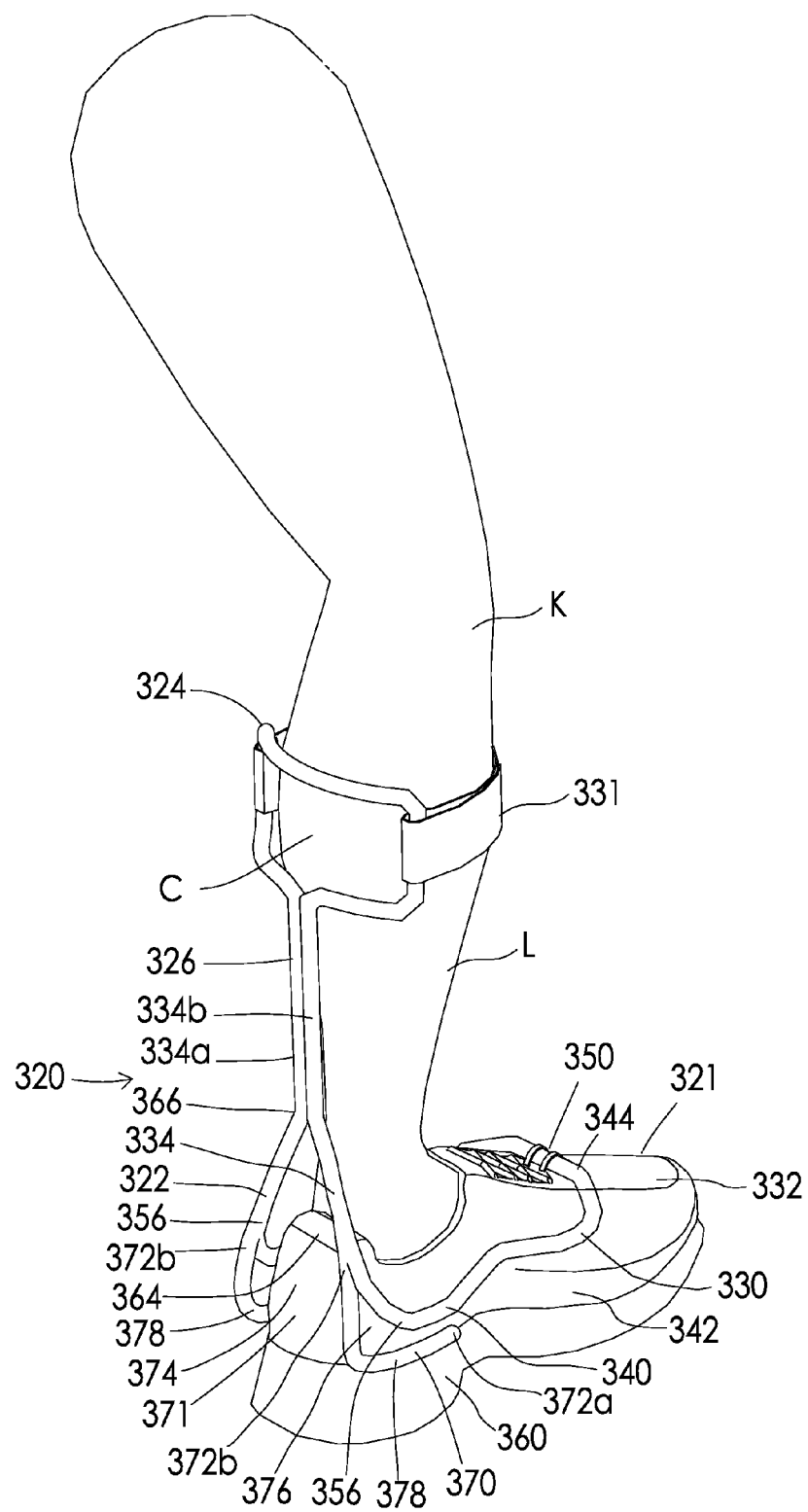
FIG. 20 is a rear perspective view of the orthotic foot brace shown in FIG. 18, wherein the brace is secured to the person's leg and footwear.
Figure 21:
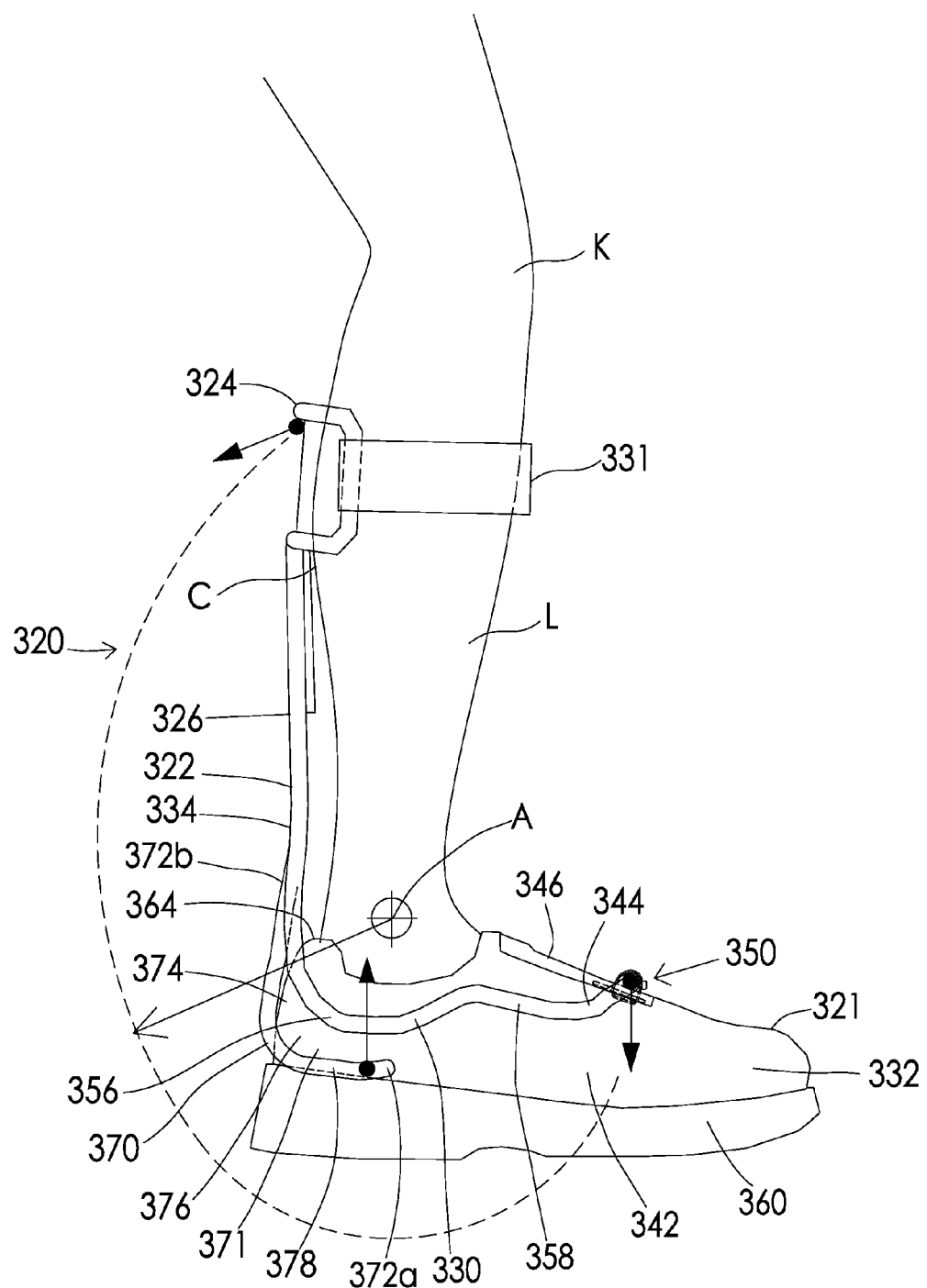
FIG. 21 is a side elevation view of the orthotic foot brace shown in FIG. 18, wherein the brace is secured to the person's leg and footwear.

Referring to FIGS. 16 and 17, there is shown that during gaiting, the brace 220 performs the same function as the brace 120 described above in reference to FIGS. 7 to 12. The heel support 270 applies a compression force on the footwear quarters 276 and restricts the plantarflexion P of the foot. The combination of the upwardly oriented force, of the rearwardly extending tension and the natural compression force applied on the lower leg L conveys the foot including the footwear 221 to return to its normal, resting position during gaiting.

Referring now to FIGS. 18 to 21, there is shown another embodiment wherein the features are numbered with reference numerals in the 300 series which correspond to the reference numerals of the previous embodiments. As it will be described in more details below, the frame 322 of the orthotic foot brace 320 differs from the frames 22, 122, 222 of braces 20, 120, 220 shown in FIGS. 1 to 17. As braces 120, 220, the brace 320 includes a heel support 370 having two spaced-apart heel support sections 378 and, more particularly, a median heel support section extending on the median side 342 of the footwear 321 and a lateral heel support section extending on the lateral side 338 of the footwear 321. Each heel support section 378 extends from the curved shaped section 356 of the frame 322 towards the toe section 332. A first end 372b of each one of the heel support sections 378 is secured to the foot section 330 of the brace 320 and the second end 372a of each one of the heel support section 378, opposed to the first end 372b, is free and is juxtaposed to either the lateral or median sides 338, 342 of the footwear 372. The free ends 372a are located close to the inner arches of the footwear 321, above the outsole 360. A section of each one of the heel support sections 378, extending from the free end 372a towards the opposed end 372b, follows a junction of an upper end of the outsole 360 and a lower end of the footwear quarters 376.

As for the above-described heel supports 170, 270, the heel support sections 378 apply a compression force on the footwear quarters 376 which maintains the heel support 370 in contact with the footwear 321 and substantially prevents or reduces its displacement relatively to the footwear 321. The heel support 370 acts as a retaining member by restraining a rearwardly and downwardly oriented pivotal movement of the brace 320 and, more particularly, at restraining a downward movement of the lower leg holder 324, of the vertical section 326, and/or of the curved shaped section 356 during gaiting.

Referring to FIGS. 16 and 17, there is shown that during gaiting, the brace 320 performs the same function as braces 120, 220 described above in reference to FIGS. 7 to 17. Furthermore, when disengaged from the lower leg L, the vertical strut 326 extends forwardly towards the toe section 332 of the footwear 321. Thus, a compression stress is applied to the person's lower leg L when engaged with the brace 320 to restrict the plantarflexion P of the foot and create a bias for the dorsiflexion D of the foot.

As for the above-described braces 20, 120, 220, the brace 320 is entirely located outside of the footwear 321, i.e. it is juxtaposed to an outer surface of the footwear 321. For conciseness, only the left foot brace which is securable to the person's left lower leg is shown and described below. For this embodiment, the right foot brace is a mirror image thereof.

In the embodiments shown, the heel support is attached to the lateral and median sections of the frame member. However, in alternative embodiments, the heel support and the lateral and median sections of the frame member can be single piece.

The braces 20, 120, 220, 320 are located outwardly of the footwear 21, 121, 221, 321 and are juxtaposed to the footwear outer surface. Thus, both shoes can be of the same size and no friction during gaiting is applied directly to the person's foot. It is adapted to fit on most conventional shoes. It is appreciated that the attachment means can be adapted to fit on any appropriate shoe. Furthermore, the braces 20, 120, 220, 320 are adapted for sports such as running.

The brace frame can be made of several materials. For instance and without being limitative, it can be made of rigid, strong, relatively light-weight polymer materials such as thermoplastic or thermosetting polymer, plastic, fiber reinforced plastic, molded chopped fibers, laminates or any other suitable material. Other suitable materials can include metals and alloys. Exemplary materials include, but are not limited to, nylons, glass filled nylon, polypropylenes, vinyls, polyvinyl chlorides, high density polyethylene, epoxies, urethanes, and polyesters. Carbon/graphite fiber materials can also be used because of their relatively high strength and their relatively low weight.

As mentioned above, the shape of the frame member can differ from the one shown in the above described embodiments. The cross-sectional shape of the frame member can be substantially flat or any other appropriate shape instead of being circular. It can be also be thicker, narrower, larger, etc. It can be discontinuous, i.e. it can include several juxtaposed and attached components. The frame member can be one single piece in the vertical section instead of two juxtaposed frame member sections.

The braces can be easily detached from the person's lower leg and footwear and remove. Further, since the brace is juxtaposed to the outer surface of the footwear and is not inserted in the inner space of the footwear, foot wounds are prevented.

In an alternative embodiment, the brace length, either in the vertical section or in the foot section, can be adjustable. For instance and without being limitative, the frame can include sliding components such as two frame member slidingly attached to one another.

The frame components such as the heel support can include anti-slip coating or features to further restrain the rearwardly and downwardly oriented pivotal movement of the brace. The brace and the footwear can included complementary Velcro members as anti-slip features. The brace can include adhesive coatings. It can also include nails or screws for securing at least sections thereof to the footwear. Furthermore, sections of the frame can include compressible material such as foam or neoprene to facilitate fitting to a person's lower leg and footwear.

Several alternative embodiments and examples have been described and illustrated herein. The embodiments of the invention described above are intended to be exemplary only. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the spirit of the invention. The scope of the invention is therefore intended to be limited solely by the scope of the appended claims.

The invention claimed is:

1. An orthotic foot brace for use on a person having a lower leg leading to a foot wearing a footwear, the orthotic foot brace comprising:
    a lower leg holder attachable around the lower leg of the person for use;
    a lower leg strut secured to the lower leg holder and capable of extending downwardly towards the footwear during use;
    a foot strut having an elongated rod secured to the lower leg strut, capable of extending therefrom along a side of the footwear, outwardly thereof, and leading to a curved footwear-attached front section having an attachment securable to an instep section of the footwear, at a location above a foot of the user when the lower leg holder is secured to the lower leg, the lower leg strut extends downwardly towards the footwear, and the middle section of the foot strut extends along the side of the footwear, outwardly thereof; and
    at least one brace retaining member secured to the foot strut and capable of being juxtaposed to the footwear during use, with at least a section capable of extending on the median side of the footwear and at least a section capable of extending on the lateral side of the footwear, outwardly thereof, and cooperating with the lower leg holder, lower leg strut, foot strut and front section in resiliently restraining a rearwardly oriented pivotal movement of the brace; wherein the lower leg strut has a distal end capable of being located above the footwear and spaced-apart therefrom and the foot strut comprises a lateral section capable of extending on a lateral side of the footwear and a median section capable of extending on a median side of the footwear, spaced-apart from the lateral section and connecting at the distal end of the lower leg strut, during use.

2. An orthotic foot brace as claimed in claim 1, wherein the at least one brace retaining member is capable of extending from the median side of the footwear to the lateral side of the footwear, during use.

3. An orthotic foot brace as claimed in claim 1, wherein the brace retaining member is capable of abuttingly receiving the footwear upon said rearward pivotal movement.

4. An orthotic foot brace as claimed in claim 1, wherein the lower leg strut is capable during use, upon said rearwardly oriented pivotal movement of the brace, of applying a forwardly oriented pressure on the lower leg, and at least a portion of the orthotic foot brace is resiliently deformed to thereafter restore the foot toward its original position.

5. An orthotic foot brace for use on a person having a lower leg leading to a foot wearing a footwear, the orthotic foot brace comprising:
    a lower leg holder attachable around the lower leg of the person for use;
    a lower leg strut secured to the lower leg holder and capable of extending downwardly towards the footwear during use;
    a foot strut having an elongated rod secured to the lower leg strut, capable of extending therefrom along a side of the footwear, outwardly thereof, and leading to a curved footwear-attached front section having an attachment securable to an instep section of the footwear, at a location above a foot of the user when the lower leg holder is secured to the lower leg, the lower leg strut extends downwardly towards the footwear, and the middle section of the foot strut extends along the side of the footwear, outwardly thereof; and at least one brace retaining member secured to the foot strut and capable of being juxtaposed to the footwear during use, with at least a section capable of extending on the median side of the footwear and at least a section capable of extending on the lateral side of the footwear, outwardly thereof, and cooperating with the lower leg holder, lower leg strut, foot strut and front section in resiliently restraining a rearwardly oriented pivotal movement of the brace; wherein the at least one brace retaining member comprises a heel support capable of extending rearwardly of the footwear during use, with two opposed ends, at least one of the two opposed ends being secured to the foot strut.

6. An orthotic foot brace as claimed in claim 5, wherein the heel support contours quarters of the footwear and extends above an outsole of the footwear.

7. An orthotic foot brace as claimed in claim 6, wherein the heel support compresses the footwear quarters when engaged with the footwear.

8. An orthotic foot brace as claimed in claim 5, wherein the foot strut has two elongated rods, each for extending along a respective side of the footwear and connecting at the front section, and the two opposed ends are attached to a respective one of the elongated rods.

9. An orthotic foot brace as claimed in claim 5 wherein the heel support is in the form of a curved rod.

10. An orthotic foot brace as claimed in claim 5, wherein the at least one brace retaining member is capable of extending from the median side of the footwear to the lateral side of the footwear, during use.

11. An orthotic foot brace as claimed in claim 5, wherein the lower leg strut is capable during use, upon said rearwardly oriented pivotal movement of the brace, of applying a forwardly oriented pressure on the lower leg, and at least a portion of the orthotic foot brace is resiliently deformed to thereafter restore the foot toward its original position.

12. An orthotic foot brace as claimed in claim 5, wherein the brace retaining member is capable of abuttingly receiving the footwear upon said rearward pivotal movement.

13. An orthotic foot brace for use on a person having a lower leg leading to a foot wearing a footwear, the orthotic foot brace comprising: a frame including a lower leg holder securable to the lower leg of the person for use; a vertical section secured to the lower leg holder and capable of extending downwardly towards the footwear during use; a foot section having an elongated rod having a having a rear section secured to the vertical section, a middle section capable of extending on one side of the footwear, outwardly of the footwear, and a curved footwear-attachment section at the front, capable of extending above an instep section of the footwear and attachable to the instep section above the footwear during use; and a brace retaining member secured to the foot section, capable of extending externally of the footwear between a median side of the footwear and a lateral side of the footwear, and resiliently restraining a rearwardly oriented pivotal movement of the brace during use wherein the brace retaining member comprises a heel support capable of extending rearwardly of the footwear during use with at least one of the two opposed ends secured to the foot section.

14. An orthotic foot brace as claimed in claim 13, wherein the brace retaining member is capable of being juxtaposed to the footwear and extending outwardly thereof during use.

15. An orthotic foot brace as claimed in claim 13, wherein the foot strut has two elongated rods, each for extending along a respective side of the footwear and connecting one another at the footwear-attachment section, and the two opposed ends are attached to a respective one of the elongated rods.

16. An orthotic foot brace as claimed in claim 13, wherein the heel support is capable of contouring the footwear quarters, extending above the outsole, and compressing the footwear quarters when engaged with the footwear.

17. An orthotic foot brace as claimed in claim 13, wherein the vertical section is capable of applying a forwardly oriented pressure on the lower leg when engaged therewith.

18. An orthotic foot brace as claimed in claim 13, further comprising an attachment capable of securing the front portion to laces of the footwear for use.

19. An orthotic foot brace as claimed in claim 13 wherein the heel support is in the form of a curved rod.

20. An orthotic foot brace for use on a person having a lower leg leading to a foot wearing a footwear, the orthotic foot brace comprising: a frame including a lower leg holder securable to the lower leg of the person for use; a vertical section secured to the lower leg holder and capable of extending downwardly towards the footwear during use; a foot section having an elongated rod having a having a rear section secured to the vertical section, a middle section capable of extending on one side of the footwear, outwardly of the footwear, and a curved footwear-attachment section at the front, capable of extending above an instep section of the footwear and attachable to the instep section above the footwear during use; and a brace retaining member secured to the foot section, capable of extending externally of the footwear between a median side of the footwear and a lateral side of the footwear, and resiliently restrainmg a rearwardly oriented pivotal movement of the brace during use, wherein the attachment includes a spreader plate and at least one attachment member capable of attaching the spreader plate, the front portion, and the laces of the footwear together.

* * * * *